United States Patent
Mase et al.

(10) Patent No.: US 9,186,079 B2
(45) Date of Patent: Nov. 17, 2015

(54) SYSTEM FOR MEASURING A PEAK FREQUENCY OF A SIGNAL FOR ANALYZING CONDITION OF A SUBJECT

(75) Inventors: Atsushi Mase, Fukuoka (JP); Daisuke Nagae, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 740 days.

(21) Appl. No.: 13/585,251

(22) Filed: Aug. 14, 2012

(65) Prior Publication Data

US 2013/0043886 A1 Feb. 21, 2013

Related U.S. Application Data

(63) Continuation of application No. PCT/JP2011/053028, filed on Feb. 14, 2011.

(30) Foreign Application Priority Data

Feb. 15, 2010 (JP) ................................ 2010-030225

(51) Int. Cl.
  G01R 27/32 (2006.01)
  A61B 5/04 (2006.01)
  (Continued)

(52) U.S. Cl.
  CPC ............... *A61B 5/0245* (2013.01); *A61B 5/021* (2013.01); *A61B 5/02405* (2013.01); *A61B 5/05* (2013.01); *A61B 5/0507* (2013.01); *A61B 5/165* (2013.01); *A61B 5/18* (2013.01); *G01R 23/16* (2013.01)

(58) Field of Classification Search
  CPC ........ A61B 5/18; A61B 5/0507; A61B 5/021; A61B 5/02405; A61B 5/165; A61B 5/024; A61B 5/0245; A61B 5/048; A61B 5/05; G01R 23/16

USPC .................................... 324/642; 600/509, 513
  See application file for complete search history.

(56) References Cited

U.S. PATENT DOCUMENTS

2004/0092835 A1\* 5/2004 Yasushi et al. ................ 600/513
2007/0109177 A1\* 5/2007 Baath et al. ................... 342/124

FOREIGN PATENT DOCUMENTS

JP 2001-095769 A 4/2001
JP 2005-218595 A 8/2005
(Continued)

OTHER PUBLICATIONS

Imuta, Hayato, et al., "Non-Contact Heart Rate Monitoring Using Micro-Wave Radar and Evaluation of the Mental Stress—an Attempt to Measure the Heart Rate Variability Without Electrodes and Through the Back of a Chair," Journal, 2008, pp. 19-23, vol. 40, Suppl. 1, Japan.

*Primary Examiner* — Amy He
(74) *Attorney, Agent, or Firm* — Dingman, McInnes & McLane, LLP

(57) ABSTRACT

A system for measuring a peak frequency of a signal applies a Maximum Entropy Method (MEM) to the signal obtained through transmission and reception of an electromagnetic wave to a subject to obtain a frequency of a peak component to be measured, thus permitting to make an appropriate assessment on a state of the subject. A signal analysis unit performs a spectrum estimation utilizing the MEM applied to a signal part of the phase difference signal with a predetermined short analysis duration, from a phase difference signal obtained by an electromagnetic wave transmitting and receiving unit, to obtain a frequency indicative of occurrence frequency of the peak component, and conducts repeatedly the same process, while shifting a position to be analyzed, corresponding to the analysis duration, thus introducing continuously the frequency. It is therefore possible to know a transition with time of the frequency of the peak component.

9 Claims, 17 Drawing Sheets

(51) Int. Cl.
*A61B 5/0245* (2006.01)
*G01R 23/16* (2006.01)
*A61B 5/021* (2006.01)
*A61B 5/024* (2006.01)
*A61B 5/05* (2006.01)
*A61B 5/16* (2006.01)
*A61B 5/18* (2006.01)

(56) References Cited

FOREIGN PATENT DOCUMENTS

| | | |
|---|---|---|
| JP | 2008-099876 A | 5/2008 |
| JP | 2008-253538 A | 10/2008 |
| JP | 2009-018091 | 1/2009 |

* cited by examiner

SYSTEM FOR MEASURING A PEAK FREQUENCY OF A SIGNAL FOR ANALYZING CONDITION OF A SUBJECT

RELATED APPLICATIONS

This patent application is a continuation of International Application No. PCT/JP2011/053028, filed on Feb. 14, 2011, entitled, "Peak Frequency Measurement System for Subject-State Analyzing Signal," which claims priority to Japanese Patent Application No. 2010-030225, filed on Feb. 15, 2010, the contents and teachings of each of which are hereby incorporated by reference in their entirety.

FIELD

The present invention relates to a system for measuring a peak frequency of a signal for analyzing condition of a subject, which system permits to obtain a frequency of a peak component of a predetermined signal based on a reflected wave caused by irradiating an electromagnetic wave to the subject, in order to analyze the condition of the subject.

The "subject" to be examined in change of the condition by irradiating the electromagnetic wave is not limited only to a biological body such as a human, an animal, etc. having substantially the stationary condition change as a so-called vital signs, but includes an object such as a machine, an apparatus, etc., which causes substantially the stationary change (movement, vibration, flowage, etc.), thus representing a broad concept.

BACKGROUND

A heartbeat to be measured in order to confirm the health of a human is expected not only to serve as a health monitor, but also to be applied to assessment of stress, a predictive detection of hypnagogic state, when driving a vehicle, or the like. More specifically, it is recognized that, since a rhythm adjustment of the heartbeat may be made by an autonomic nerve, an analysis of change in heartbeat interval permits to estimate an influence of the autonomic nerve on the heartbeat, and a mental stability and a degree of stress, which may cause such a change.

For example, a condition, which forces an operator or a driver to take a seat for a long period of time along with an operation of a computer or a driving of a vehicle for a long period of time, or a long-distance movement, may give the operator or driver a mental load (stress). There have conventionally been problems that such a mental load may sometime cause various kinds of stress-related illness. It has been significant to properly evaluate the stress applied to the human body to avoid such a illness in advance, and there has been proposed an approach to evaluate the stress through analysis of heartbeat variability.

A way to attach electrodes to a body of a subject to obtain an electrocardiogram has conventionally generally been taken to measure the heartbeat. The heartbeat variability may be calculated by reading out peak intervals (RRI) of R-waves appearing in a shape of spike in the cardiac electrogram based on a threshold value as set. A frequency analysis of such a heartbeat variability permits to provide a stress evaluation index.

More specifically, a frequency analysis of time variation of the heartbeat results in the fact that the spectrum peak appears in each of the low frequency component having the bandwidth of from about 0.03 Hz to about 0.15 Hz and the high frequency component having the bandwidth of from 0.15 Hz to about 0.45 Hz. The respective peak values will be referred to as "LF" and "HF", respectively. LF represents a state of activity of both of the sympathetic nerve and the parasympathetic nerve, and HF represents a state of activity of only the parasympathetic nerve. Here, in view of the facts that the sympathetic nerve predominates in a state in which a human body is subject to stress, and the parasympathetic nerve conversely predominates in a state of relaxation, a value of LF/HF may be deemed as an index of activity of the sympathetic nerve, namely as a stress evaluation value. When values of integral of frequency spectrums of from 0.03 to 0.15 Hz and from 0.15 to 0.45 Hz are referred to as "LF" and "HF", respectively, a value of LF/HF may be deemed as an index.

Concerning an example of the conventional method to make a stress evaluation based on variation of heartbeat interval in this manner, JP 2001-95769 A, JP 2005-218595 A and JP 2008-99876 A disclose such a method.

JP 2008-253538 A discloses an example of a method in which a heartbeat is measured in a non-contact state with the use of a microwave and then a stress evaluation is made, in a different manner from the method utilizing the electrocardiograph. This publication describes a method comprising the steps of irradiating radio wave to a subject, receiving a reflected wave from the subject, converting a signal as received into a digital signal, calculating a peak interval (a PP interval) of the signal, and analyzing a heart rate variability (HRV) index from the PP interval based on an approach such as a Maximum Entropy Method to provide a low frequency component and a high frequency component as separated of the frequency region.

SUMMARY

Each of these patent publications discloses a conventional system of measuring and evaluating the heartbeat interval. However, there are involved problems that, since a measurement is made by bringing electrodes for measurement into a direct contact with a subject when a heartbeat is measured by an electrocardiograph to obtain the heartbeat variability, the subject is given another stress such as the subject having a feeling of restraint or being more aware of measurement, and an accurate stress evaluation may not be made based on the heartbeat variability as obtained.

On the other hand, a proposal of measuring a heartbeat in a non-contact state with the use of a microwave is made as described in JP 2008-253538 A indicated above. This permits to remove a stress factor caused by a direct contact of a measurement device with a subject when making the measurement.

However, JP 2008-253538 A indicated above discloses no specific technical matters to obtain information indicative of the heartbeat variability such as a PP interval, a heartbeat variability index, etc. from the signal obtained by receiving the reflected wave from the subject. Especially, the signal obtained by receiving the reflected wave of the microwave may include noise components, which are not to be measured, such as a random motion of the subject, a body motion caused by breathing, or the like. However, motion of a heart or an artery appearing on the surface of a body of the subject is extremely small in comparison with the above-mentioned noise, with the result that, in most cases, the heartbeat interval may not clearly be revealed in the signal, unlike the electrocardiogram. In spite of such circumstances that the signal peak interval cannot be read out in an easy manner, JP 2008-253538 A indicated above includes no specific detailed technical description to enable information on the variation of the heartbeat interval to be extracted appropriately, thus involving a problem of difficulty in carrying out the invention.

The Maximum Entropy Method (MEM), which is described in JP 2008-253538 A indicated above as a method of analyzing a heart rate variability (HRV) index to provide a low frequency component and a high frequency component as separated of the frequency region, has a feature that a spectrum can be calculated even from data in a small duration in an extremely high frequency resolution capability. It is therefore known not only that the Maximum Entropy Method (hereinafter referred to as "MEM") can be used for a spectrum analysis of a stationary signal, but also that the MEM is executed on non-stationary experimental data each small duration to make an application to follow a substantially non-stationary spectrum variation.

A spectrum estimation made based on the MEM is conducted by the steps of evaluating first an auto-regressive model of an analysis signal, and then making a spectrum estimation based on the resultant. On this occasion, a selection of an order of the auto-regressive model (hereinafter referred to as the "model order") is of the upmost importance. When the model order as selected is excessively small, a spectrum estimation value is smoothed and a spectrum peak, which originally exists, may not be detected properly. When the model order is excessively large in an opposite manner, many spurious peaks may appear at small intervals on the evaluated spectrum. Under such circumstances, although a selection (estimation) of an appropriate model order is necessitated, such a selection is extremely difficult, since the appropriate model order depends on a form of signal.

As a model order estimation method as generally applied, there have been a Final Prediction Error (FPE) method, an Akaike's Information Criterion (AIC) method, or the like. However, the appropriate model order, which may be selected by such a method, is generally of an extremely small value, with the result that the spectrum may be smoothed markedly, there may be a high risk that peaks in the frequency region, which are to be noted, may not be revealed. Therefore, such known order estimation methods are not adequate to analysis of a multispectral structure. When only a part of the frequency region is to be noted like analysis of the heart-rate frequency, for a subject having measurement data with a multispectral structure in a manner of analysis of a heartbeat frequency, such an order estimation method does not work appropriately, with the result that a selection of the appropriate model order may not be made, thus making it difficult to apply actually the MEM. This sort of thing contributes to no appearance of specific analysis examples in the field of the above-mentioned stress assessment in the past.

An object of the present invention, which was made to solve the above-mentioned problems, is therefore to provide a system for measuring a peak frequency of a signal, in which system an MEM is applied to a signal obtained by transmitting and receiving an electromagnetic wave relative to a subject, a frequency of a peak component to be measured is obtained to receive a predetermined information, while avoiding influence by a noise, thus making it possible to make an appropriate assessment on condition of the subject.

A system according to the present invention for measuring a peak frequency of a signal for analyzing condition of a subject, comprises: an electromagnetic wave transmitting and receiving unit that irradiates a continuous electromagnetic wave having a predetermined frequency to a subject, receives a reflected wave from the subject, and outputs a phase difference signal between an irradiation wave and the reflected wave; and a signal analysis unit that obtains, with a spectrum estimation utilizing a Maximum Entropy Method with a predetermined analysis duration, a frequency indicative of a occurrence frequency of a peak component of a signal, which is included by the phase difference signal between the irradiation wave and the reflected wave, and is generated substantially periodically in accordance with substantially the stationary change of the subject to be measured, and conducts repeatedly a process of calculating the frequency on a time axis of the phase difference signal.

According to the present invention, the signal analysis unit executes the spectrum estimation utilizing the Maximum Entropy Method for a part of the phase difference signal, which is obtained by the electromagnetic wave transmitting and receiving unit, and may include peak components to be measured and noises, which are not to be done, with a predetermined short analysis duration, to obtain the frequency indicative of the occurrence frequency of the peak component, from the above-mentioned phase difference signal, and conducts repeatedly the process of calculating the frequency on a time axis of the phase difference signal, while shifting a position to be measured, corresponding to an analysis duration, thus introducing continuously the frequency. It is therefore possible to know a transition with time of the frequency of the peak component. As a result, it is possible to derive effectively a state of variation of the peak component to be measured, even in case where the signal obtained by the electromagnetic wave transmitting and receiving unit includes a noise so that the peak component to be measured is not clearly revealed.

The system according to the present invention for measuring a peak frequency of a signal for analyzing condition of a subject, may comprise, where appropriate, a conversion unit to which the frequency of the peak component calculated by the signal analysis unit is input, and which derives an occurrence time interval of the peak component based on a reciprocal of the frequency.

According to the present invention, the signal analysis unit obtains the frequency of the peak component to be measured from the above-mentioned phase difference signal, which is obtained by the electromagnetic wave transmitting and receiving unit, the conversion unit derives the time interval of the peak component based on the reciprocal of the frequency, and the time interval of the peak component is also continuously derived along with the deriving of the frequency, which is repeated in accordance with the obtainment of the phase difference signal. It is therefore possible to know a transition with time of the time interval of the peak component, i.e., the variation in time of the interval. As a result, it is possible to derive effectively the variation of interval of the peak component to be measured, even in case where the signal obtained by the electromagnetic wave transmitting and receiving unit includes a noise so that the peak component to be measured is not clearly revealed, thus permitting an appropriate assessment based on the variation of interval. For example, in case where the heartbeat is to be measured, it is possible to derive successively the heartbeat interval to obtain a heartbeat interval variation (HRV) in a short period of time and a stress assessment, etc. utilizing this heat-rate interval variation can also be made in a short period of time.

The system according to the present invention for measuring a peak frequency of a signal for analyzing condition of a subject, may have, where appropriate, a configuration that the signal analysis unit conducts repeatedly the spectrum estimation with the analysis duration relative to the phase difference signal, while shifting, in each spectrum estimation, sequentially an analysis range by a predetermined shifted time from a signal start side toward a direction of a passage of time.

According to the present invention, the signal analysis unit conducts the spectrum estimation with a sufficiently short shifted time, by applying, for the phase difference signal obtained by the electromagnetic wave transmitting and receiving unit, the Maximum Entropy Method to the part of the signal within the analysis duration range to obtain the time variation of the peak frequency, and repeating this step while shifting the analysis time duration by the shifted time. This makes it possible to increase fully the number of samples of the frequency of the peak component to be measured, as obtained for the phase difference signal. In case where an analysis is made separately based on the frequency of the peak component as obtained, it is possible to find out surely the variation state of the peak component to be measured, thus permitting an appropriate assessment on this variation state.

The system according to the present invention for measuring a peak frequency of a signal for analyzing condition of a subject, may have, where appropriate, a configuration that the signal analysis unit sets, for a predetermined frequency range provided as a frequency bandwidth required for an evaluation with a frequency analysis to be conducted subsequently for the peak component of the signal to be measured, which has been derived by the signal analysis unit, the shifted time as a maximally long period of time within a range of time, which is obtained as a reciprocal of a frequency higher than twice a highest frequency in the predetermined frequency range.

According to the present invention, the shifted time based on which the analysis duration is set, is maximized within the period of time, which is obtained as the reciprocal of the frequency higher than twice the frequency required for the evaluation of the peak component of the signal to be measured. It is therefore possible to ensure a sampling frequency required for enabling the variation in the frequency region for which a subsequent evaluation is to be made, to be reproduced in a sampling process. Accordingly, the number of the spectrum evaluation process can be controlled, while ensuring a state in which the variation in the frequency region as required for evaluation of the peak component to be measured is reproduced in the sampling process to find out surely the variation in the frequency analysis, so as to enable the frequency of the peak component to be extracted in series in an instantaneous manner from the input of the phase difference signal, without causing a serious process delay by time lag in each steps, thus ensuring promptness of the analysis.

The system according to the present invention for measuring a peak frequency of a signal for analyzing condition of a subject, may have, where appropriate, a configuration that the signal analysis unit obtains a frequency power spectrum with the spectrum estimation with the analysis duration by the Maximum Entropy Method, and determines, as a frequency of the peak component to be obtained, a frequency having a maximum peak value in a known frequency range of the frequency power spectrum, the frequency having the maximum peak value corresponding to a frequency bandwidth of the peak component to be measured, which is actually applicable.

According to the present invention, in view of the fact that the frequency power spectrum is required for the spectrum estimation in the analysis duration of the phase difference signal, there is used, as a representative value, the frequency of the maximum spectrum peak in the known range corresponding to the frequency bandwidth of the peak component to be measured, which is actually applicable, and the peak frequency is obtained. It is therefore possible to detect surely the frequency peak corresponding to the timing of appearance of the peak component to be measured, and prevent a peak or a spurious peak caused by a variation excepting a phenomenon, which causes the peak component to be measured, from being estimated wrongly as the frequency corresponding to the peak component of the signal to be measured.

The system according to the present invention for measuring a peak frequency of a signal for analyzing condition of a subject, may have, where appropriate, a configuration that the signal analysis unit conducts the spectrum estimation utilizing the Maximum Entropy Method for the phase difference signal, by estimating an auto-regressive model of the peak component to be measured, setting an auto-regressive model order as a value within a predetermined range and conducting a spectrum estimation based on the model; the signal analysis unit previously conducts a simulation utilizing a signal model including an ideal peak component to determine at least a minimum value of a range of the model order; the simulation utilizing the signal model including the ideal peak component is conducted by: providing a plurality of patterns of the signal model having respectively different peak frequencies by adding the peak frequency in the model signal, which has a time window of a predetermined period of time and includes the ideal peak component to be measured, in a plurality of frequencies in a shifted manner by a predetermined frequency within the known frequency range corresponding to the frequency bandwidth of the peak component to be measured, which is actually applicable; providing a plurality of analysis durations during which the spectrum estimation is to be applied, the analysis durations being different from each other within a range of the time window; and conducting the respective spectrum estimation while using a number of data point, which is a product of the analysis duration and a sampling frequency, as a maximum value of the model order and varying the model order from 1 to a maximum value in a combination of each the signal model and each the analysis duration, detecting an existence of a spectrum peak in the known frequency range corresponding to the frequency bandwidth of the peak component to be measured, which is actually applicable, and determining, as an effective model order, the model order in case where the spectrum peak exists; and the signal analysis unit determines, as a minimum value within a range of the model order as provided, which is to be used in the spectrum estimation with respect to the phase difference signal, a maximum one throughout all of minimum vales of the effective model orders in the respective combination of each the signal model and each the analysis duration, as obtained by the simulation.

According to the present invention, when setting the auto-regressive model in the spectrum estimation based on the Maximum Entropy Method, the simulation utilizing the signal model including the ideal peak component corresponding to the peak component to be measured is conducted; the existence of the spectrum peak is confirmed, while changing the model order for a number of conditions of combination of the different signal models of the peak frequency and the plurality of analysis durations; the minimum value of the model orders is obtained from the effective model orders in which the spectrum peak exists; and the model order is set within the model setting range by deeming the maximum model order in the minimum values as obtained, as the minimum value within the model order setting range. This makes it possible to avoid surely a prospect that the estimation itself cannot be made in the spectrum estimation utilizing the model order, thus permitting to extract the frequency of the peak component to be measured through the spectrum estimation, without causing any problem.

The system according to the present invention for measuring a peak frequency of a signal for analyzing condition of a subject, may have, where appropriate, a configuration that the spectrum peak existing in response to the effective model order in the simulation by the signal analysis unit is used as an estimated peak frequency of the model order; the signal analysis unit calculates, for the effective model orders in the respective combination of each the signal model and each the analysis duration, as obtained by the simulation, an estimation error of the respective estimated peak frequency for the respective model orders relative to the frequency of the signal model, and extracts, as a representative model order, a minimum one of the model orders having the estimated peak frequencies in case where the estimation error becomes smallest; the respective representative model orders are compiled for a same analysis duration and averaged, and an averaged value for the respective analysis duration is obtained as an averaged model order; and when the averaged model orders are represented in a two-dimensional graph in which the analysis duration is a first axis and the model order is a second axis, a value of the single model order forming a straight line, which is most approximate to a line indicative of the averaged model order on the graph, is used as an optimum value of the model order to be used in the spectrum estimation with respect to the phase difference signal.

According to the present invention, the estimation error of the respective estimated peak frequency for the respective model orders is calculated for the effective model orders in the respective combination of each the signal model and each the analysis duration, as obtained through the simulation by the signal analysis unit; the minimum one of the model orders in case where the estimation error becomes smallest is compiled for the same analysis duration and the compiled are averaged; and the value of the model order, which is most approximate to the average value of the model order in the respective analysis duration, is used as the optimum value of the model order, thus extracting the frequency of the peak component. This makes it possible to prevent appearance of spurious peaks, even if the spectrum estimations are conducted with various kinds of analysis durations as set, and detect correctly the spectrum peak, which should exist in the known frequency range to be noted, thus permitting to provide an accurate frequency with a small error for the frequency to be actually measured.

The system according to the present invention for measuring a peak frequency of a signal for analyzing condition of a subject, may have, where appropriate, a configuration that the signal analysis unit conducts the spectrum estimation utilizing the Maximum Entropy Method for the phase difference signal, by estimating an auto-regressive model of the peak component of the signal to be measured, setting an auto-regressive model order as a value within a predetermined range and conducting a spectrum estimation based on the model; the signal analysis unit previously conducts a simulation utilizing a signal model including an ideal peak component to determine at least a lower value of a range of the model order; the simulation utilizing the signal model including the ideal peak component is conducted by: providing a plurality of patterns of the signal model having respectively different peak frequencies by adding the peak frequency in the model signal, which has a time window of a predetermined period of time and includes the ideal peak component to be measured, in a plurality of frequencies in a shifted manner by a predetermined frequency within the known frequency range corresponding to the frequency bandwidth of the peak component to be measured, which is actually applicable; providing a plurality of analysis durations during which the spectrum estimation is to be applied, the analysis durations being different from each other within a range of the time window; and conducting the respective spectrum estimation while using a number of data point, which is a product of the analysis duration and a sampling frequency, as a maximum value of the model order and varying the model order from 1 to a maximum value in a combination of each the signal model and each the analysis duration, detecting an existence of a spectrum peak in the known frequency range corresponding to the frequency bandwidth of the peak component to be measured, which is actually applicable, and determining, as an effective model order, the model order in case where the spectrum peak exists; and the signal analysis unit determines, as a boundary value, a value of the analysis duration having a maximum value in the combination of the respective signal model in which no effective model order has been determined, and the respective analysis duration, as obtained by the simulation, and sets the range of the analysis duration in the spectrum estimation with respect to the phase difference signal so as to be larger than the boundary value.

According to the present invention, when setting the auto-regressive model in the spectrum estimation based on the Maximum Entropy Method, the simulation utilizing the signal model including the ideal peak component corresponding to the peak component to be measured is conducted; the existence of the spectrum peak is confirmed, while changing the model order for a number of conditions of combination of the different signal models of the peak frequency and the plurality of analysis durations; the maximum value of the analysis durations in which any effective model order having the spectrum peak has not been created, is used as the boundary value, and the analysis duration is set within a range, which is larger than the above-mentioned boundary value, thus conducting the spectrum estimation. This makes it possible to avoid surely a prospect that the estimation itself cannot be made in the spectrum estimation, which is conducted in the predetermined analysis duration, thus permitting to extract the frequency of the peak component to be measured through the spectrum estimation, without causing any problem.

The system according to the present invention for measuring a peak frequency of a signal for analyzing condition of a subject, may have, where appropriate, a configuration that the peak component of the signal to be measured represents a heartbeat of the subject; and the frequency bandwidth of the peak component to be measured, which is actually applicable, is within a range of frequency of from 0.7 Hz to 1.5 Hz, between which the heartbeat at rest in a sitting posture actually exists.

According to the present invention, in view of the fact that the frequency power spectrum is required for the spectrum estimation of the phase difference signal, which includes the peak component indicative of the heart-rate to be measured, there is obtained as the frequency to be obtained, i.e., the heart-rate frequency, the frequency of the maximum spectrum peak in the range of from 0.7 Hz to 1.5 Hz corresponding to the frequency bandwidth, between which the heartbeat at rest in a sitting posture exists. It is therefore possible to detect surely the spectrum peak corresponding to the timing of appearance of the heartbeat to be measured, to obtain the heart-rate frequency, and prevent a peak or a spurious peak caused by a variation excepting the heartbeat, from being estimated wrongly as the frequency corresponding to the heartbeat, thus permitting to obtain the heartbeat frequency with high accuracy.

DETAILED DESCRIPTION

Figure 1:
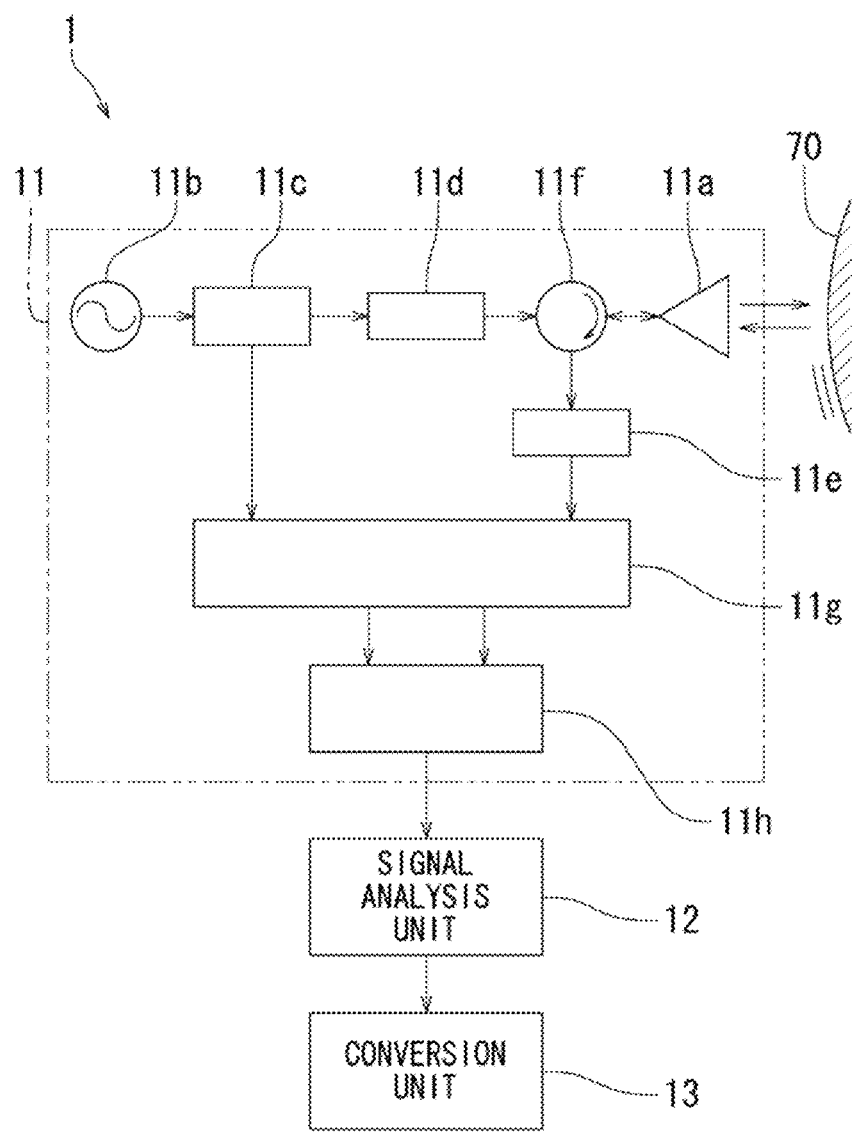
FIG. 1 is a block diagram of a system according to an embodiment of the present invention for measuring a peak frequency of a signal.
Figure 2:
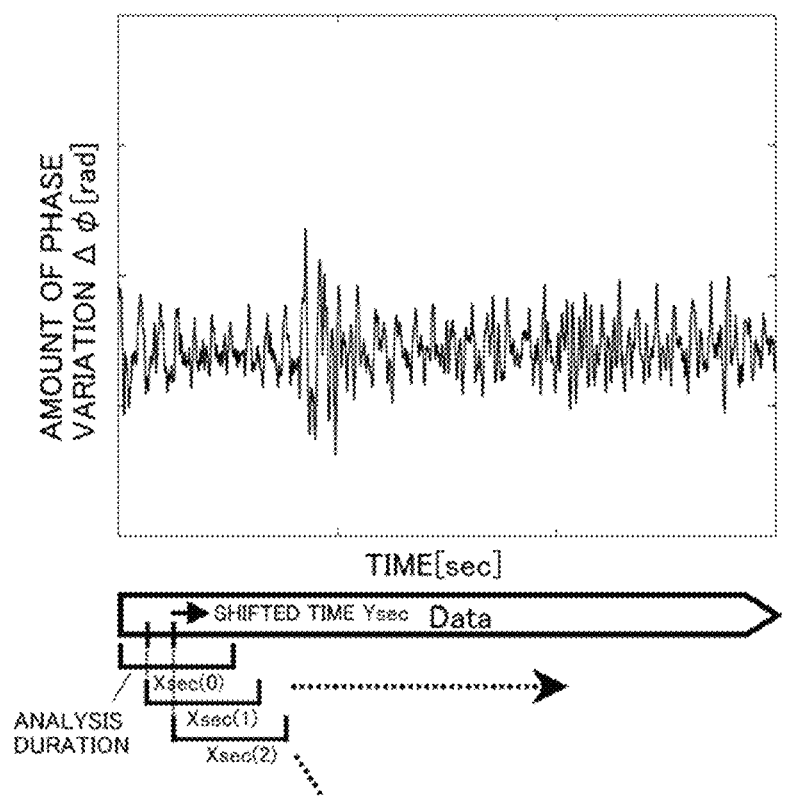
FIG. 2 is a descriptive view of a state of a repeated analysis of a phase difference signal in the system according to the embodiment of the present invention for measuring a peak frequency of a signal.
Figure 3:
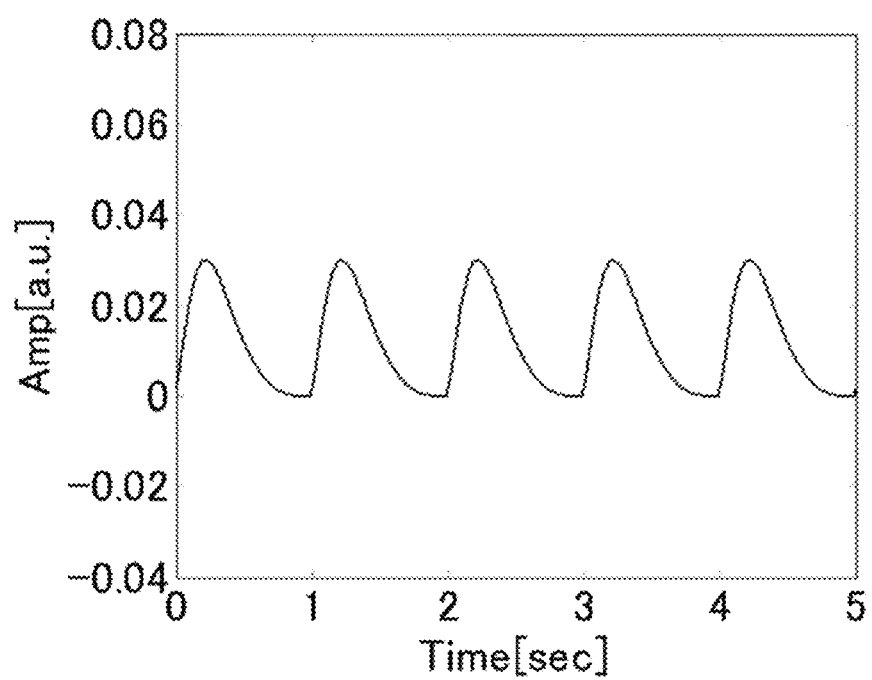
FIG. 3 is a graph of an ideal heartbeat signal model used in the system according to the embodiment of the present invention for measuring a peak frequency of a signal.

Now, a system according to the embodiment of the present invention for measuring a peak frequency of a signal will be described below with reference to FIGS. 1 to 9 as indicated above.

The system 1 according to the embodiment of the present invention for measuring a peak frequency of a signal in the respective figures as indicated above has a configuration, which comprises an electromagnetic wave transmitting and receiving unit 11 that irradiates a continuous electromagnetic wave to a subject 70, receives a reflected wave from the subject 70, and outputs a phase difference signal between an irradiation wave and the reflected wave; a signal analysis unit 12 that conducts repeatedly a process of calculating a frequency of a heartbeat to be measured, with a spectrum estimation utilizing a Maximum Entropy Method (hereinafter referred to as "MEM"), for the phase difference signal between the irradiation wave and the reflected wave; and a conversion unit 3 that obtains a heartbeat interval based on a reciprocal of the frequency of the heartbeat.

The above-mentioned electromagnetic wave transmitting and receiving unit 11 irradiates a microwave as a sinusoidal wave to the subject 70, receives a reflected wave from the subject 70, and outputs a phase difference signal between the irradiation wave and the reflected wave.

More specifically, the electromagnetic wave transmitting and receiving unit 11 comprises an antenna 11a that irradiate the microwave to the subject and receives the reflected wave, a microwave oscillator 11b that generates the microwave as the sinusoidal wave, a directional coupler 11c that separates the microwave as generated into an irradiation wave to the subject and a reference wave, an attenuator 11d that attenuates the irradiation wave, an amplifier 11e that amplifies the reflected wave, a circulator 11f that sends the irradiation wave to the antenna 11a and sends the reflected wave from the antenna 11a to the amplifier 11e, a quadrature detector 11g that utilizes the reflected wave from the amplifier 11e and the reference wave from the directional coupler 11c to conduct a quadrature detection process, and a calculation section 11h that a phase difference signal from two signals based on a phase variation obtained by the quadrature detection process.

The electromagnetic wave transmitting and receiving unit 11 utilizes a homodyne interference method, which is a method of mixing the reflected wave and the reference wave based on the same oscillator's output to detect a frequency difference and a phase difference. The microwave outputted from the microwave oscillator 11b is separated into the irradiation wave and the reference wave by the directional coupler 11c so that the irradiation wave is irradiated to a predetermined area of a human body as the subject.

In case where the antenna 11a is not capable of being placed in the vicinity of the subject and the microwave is irradiated from a remote place, the direction and the position of the antenna may be changed to follow the subject so that the irradiation wave can be irradiated to the subject who is moving, to obtain surely the reflected wave. In case where the subject is a human, the irradiation wave from the antenna 11a may be irradiated in accordance with a trajectory of motion of the human in a scanning manner in a region such as a walkway, etc. in which there is previously known that the human passes, to obtain surely the reflected wave from the human. In case where there cannot previously be predicted a place where a human as the subject exists, it may be possible to assume the place of the human based on a clue as a temperature different from a surrounding environment of a human or a voice thereof and change the position of antenna.

If the subject is moving and the subject is far away from the antenna 11a (by a distance of for example more than 10 meters) and the reflected wave signal level becomes small, a coupling from the transmitting side at the circulator 11f may be an obstacle due to the smaller signal level, in case of a transmitting and receiving shared antenna. It is therefore preferable to make the transmitting antenna and the receiving antenna independent, thus providing an improved S/N ratio.

In case where the transmitting antenna and the receiving antenna are made independent and the transmitting antenna is moved in accordance with the movement of the subject, an omnidirectional antenna may be used as the receiving antenna so as to be able to surely receive the reflected wave in which the direction from the subject who is moving changes from moment to moment.

The signal of the reflected wave, which has been reflected from the subject 70, is amplified by the amplifier 11e, and then this reflected wave and the above-mentioned reference wave, which is coincident with the irradiation wave, are mixed by the quadrature detector 11g to obtain a cosine component ($E_r \cos \Delta\phi$) and a sine component ($E_r \sin \Delta\phi$) based on the phase variation $\Delta\phi$ of the reflected wave and the reference wave, and then a calculating unit 11h calculates from the obtained value the phase difference signal, which is directly proportional to $\Delta\phi$.

The quadrature detector 11g mixes two quadrature reference wave components ($A \cos \omega t$, $A \sin \omega t$) with the signal component ($B\cos(\omega t+\Delta\phi)$) of the reflected wave to carry out a demodulation operation, thus obtaining the respective cosine and sine signal components ($E_r \cos \Delta\phi$ and $E_r \sin \Delta\phi$) of the phase variation. An amplitude component $E_r$ is a product of an amplitude A of the reference wave signal component and am amplitude B of the reflected wave signal component.

The above-mentioned calculating unit 11h utilizes the respective cosine and sine signal components ($E_r \cos \Delta\phi$ and $E_r \sin \Delta\phi$) of the phase variation $\Delta\phi$ obtained by the quadrature detector 11g to calculate the component, which is directly proportional to $\Delta\phi$ based on the following relationship:

$$\Delta\phi=\tan^{-1}(E_r \sin \Delta\phi/E_r \cos \Delta\phi)$$

and separates the amplitude (the component $E_r$) and the phase (the component $\phi$) of the signal to obtain the phase difference signal. The phase variation $\Delta\phi$ corresponds to an amount of movement of a reflection surface to be detected, with the result that the phase difference signal may change along with the variation of the reflection surface.

There may be microscopic variation of a skin or a muscle of a human along with the pulsation of a heart thereof, which is considered as substantially the stationary variation, in a predetermined part of the human body to which the microwave is irradiated, and this microscopic variation is reflected in the above-mentioned phase variation $\Delta\phi$, so that the phase difference signal as obtained may include peak components corresponding to the pulsation of the heart of the human, which is considered as substantially the stationary variation. It is possible to obtain the frequency of the heartbeat from this phase difference signal.

The electromagnetic wave transmitting and receiving unit 11 has a configuration to cause the reflected wave and the reference wave based on the output of the single microwave oscillator to adopt a homodyne method used for the phase difference detection. However, the present invention is not limited onto to such a configuration. There may be applied another configuration that, for example, two microwave oscillators are used, and a reflected wave caused by irradiating a microwave outputted from one of the oscillators to the subject and reflecting it by the surface of the subject, and a microwave outputted by the other oscillator are frequency-mixed by a mixing unit to obtain a reflected wave signal as converted into an intermediate frequency, and this reflected wave signal is outputted together with a reference wave signal as an intermediate frequency, which has been obtained by frequency-mixing the respective microwave outputs from the two oscillators by the missing unit, thus adopting a heterodyne method. The application of the two oscillators to use both the reflected wave signal and the reference wave signal in the form of the intermediate frequency makes it possible to narrow the bandwidth of a filter such as a bandpass filter, which is inserted into the respective signal line to attenuate unwanted components, and remove influence of the unwanted components in the respective signals, thus improving accuracy of measurement. In addition, outputting both the reflected wave signal and the reference wave signal as converted into the intermediate frequency makes it possible to amplify the signal in the intermediate frequency region having small noise and fluctuation, thus permitting to constitute a stable system.

In addition, there may be adopted a heterodyne method in which a single microwave oscillator is used and a high-frequency oscillator and an up-converter are used together to generate the irradiation wave and the reference wave. Although stability obtained by using the two microwave oscillators is based on superimposition of the both fluctuations, stability obtained by using the above-mentioned up-converter is determined by the fluctuation of only the high-frequency oscillator. It is therefore possible to remarkably reduce the fluctuation component, thus permitting to improve accuracy of the phase measurement.

Further, there may be adopted a configuration having an adjustment unit to adjust the signal output level of the reflected wave signal obtained by the antenna 11a to obtain the reflected wave signal within the predetermined output range, and more specifically, a so-called AGC (automatic gain control) circuit unit to detect and monitor an output from a gain variable amplifier by a detection control section and control the gain of the gain variable amplifier so as to provide a predetermined constant output.

The above-mentioned signal analysis unit 12 conducts the spectrum estimation utilizing the MEM with the predetermined analysis duration for the phase difference signal between the irradiation wave and the reflected wave to obtain, for the peak component of the signal, which is included by the above-mentioned phase difference signal and is generated substantially periodically in accordance with substantially the stationary change of the subject to be measured, the frequency indicative of the occurrence frequency of the peak component, and conducts repeatedly the process of calculating the frequency on a time axis of the phase difference signal. The thus continuously obtaining the frequency makes it possible to derive the time variation of the frequency of the above-mentioned peak component, i.e., the time variation of the heartbeat frequency.

More specifically, the signal analysis unit 12 conducts repeatedly a set of steps of estimating, after obtainment of the phase difference signal by the above-mentioned electromagnetic wave transmitting and receiving unit 11 or in parallel with obtainment of the phase difference signal, the autoregressive model of the signal of the heartbeat to be measured in accordance with the MEM, setting the appropriate conditions such as the auto-regressive model of the above-mentioned model, etc., which have previously been obtained through the simulation, conducting the spectrum estimation with the predetermined analysis duration based on the above-mentioned model, detecting, of the frequency power spectrum as estimated, the value of the frequency at the maximum peak position (the spectrum peak) in the frequency range within which the heartbeat may exist, and using the resultant as the frequency of the heartbeat, while shifting, in each spectrum estimation, sequentially the analysis range for the phase difference signal by the predetermined shifted time in the direction of a passage of time (see FIG. 2), thus obtaining the frequency with the duration of the shifted time along the time axis of the phase difference signal.

Here, the description will be given below of a process of deriving the spectrum with the MEM. The auto-regressive model relative to observation data may be expressed as follows:

$$x_k = -\sum_{i=1}^{m} a_{mi} x_{k-i} + n_k \quad (1.01)$$

wherein $x_k$ being time-series data, $n_k$, stationary white noise independent from $x_{1(<k)}$, m, auto-regressive model order, and $a_{mi}$, auto-regressive coefficient at an order m.

Here, an auto-correlation function of the time-series data $x_k$ may be expressed by the following equation:

$$R_i = R(i\Delta t) \equiv E\{x_k x_{k-i}\} \quad (1.02)$$

wherein $E\{\ \}$ being an expectation, and the auto-correlation function being as follows:

$$R_0 = E\{x_k^2\} = -\sum_{i=1}^{m} a_{mi} R_i + E\{n_k^2\} \quad (1.03)$$

$n_k$, is independent from $x_{1(<k)}$. When both sides of Equation (1.01) are multiplied by $x_{k-1, k-2 \ldots k-m}$ to take the expectation, a matrix equation as expressed by the following equation may be obtained with the use of the auto-correlation function of the respective lag:

$$\begin{bmatrix} R_0 & R_1 & \cdots & R_m \\ R_1 & R_0 & & R_{m-1} \\ \vdots & & \ddots & \vdots \\ R_m & \cdots & \cdots & R_0 \end{bmatrix} \begin{bmatrix} 1 \\ a_{m1} \\ \vdots \\ a_{mm} \end{bmatrix} = \begin{bmatrix} P_m \\ 0 \\ \vdots \\ 0 \end{bmatrix} \quad (1.04)$$

wherein $P_m$ being dispersion of the stationary white noise. Equation (1.04) is generally called "Yule-Walker equation". By applying Wiener-Khintchine formula to Equation (1.04) and solving the formula there may be obtained the following equation:

$$S(\omega) = \frac{P_m \Delta t}{\left|1 + \sum_{i=1}^{m} a_{mi} e^{-j\omega i \Delta t}\right|^2} \quad (1.05)$$

The relationship between the auto-regressive model $\{a_k\}$ and the power spectrum $S(\omega)$ may be obtained by Equation (1.05).

Therefore, the auto-regressive coefficient $a_{mi}$ and the dispersion $P_m$ may be estimated by obtaining the auto-regressive function $R_0, R_1, R_2, \ldots$ from the phase difference signal and substituting it into Equation (1.04). Substitution of them into Equation (1.05) permits to obtain the power spectrum $S(\omega)$ of the phase difference signal.

According to the spectrum estimation utilizing the MEM with the predetermined analysis duration as mentioned above by the signal analysis unit 12, of the frequency power spectrum as estimated, the value of the frequency at the maximum peak position (the spectrum peak) in the range corresponding to the frequency range within which the signal peak composition to be measured may actually exist, is estimated as the frequency of the peak composition to be measured. What is to be measured is the heartbeat. Therefore, the value of the maximum peak position within the frequency bandwidth within which the heartbeat may exist, for example, within the range of from 0.7 Hz to 1.5 Hz, between which the heartbeat of a human at rest in a sitting posture actually exists, may be estimated as the frequency of the heartbeat.

An erroneous selection of the frequency range for which a search of the maximum peak position is made may disable a detection of the appropriate peak frequency corresponding to the frequency of the heartbeat from being made, instead there may be a possibility that a position of a peak caused by a variation (motion) of a subject excepting the heartbeat or a position of a spurious peak is estimated as the frequency of the heartbeat.

The signal analysis unit 12 is required to estimate previously the auto-regressive model of the signal of the heartbeat in the spectrum estimation with the MEM and set the auto-regressive model order of this model. The model order cannot be set as a value exceeding an analysis data point number, i.e., a product of the analysis duration and the sampling frequency, and the product of this analysis duration and the sampling frequency therefore becomes the maximum value of the model order. It is preferable to make the spectrum estimation for the minimum value of the model order even if the frequency of the heartbeat of the peak component to be measured in the phase difference signal varies or the analysis duration varies. In addition, it is preferable to use the model order in which an error between the frequency as obtained and the true frequency of the heartbeat is small even when the frequency of the heartbeat and the analysis duration vary, and the model order having the smallest error is used as the optimum value of the model order. When the model order is excessively small, a spectrum estimation value is smoothed and a spectrum peak, which originally exists, may not be detected properly. When the model order is excessively large in an opposite manner, many spurious peaks may appear at small intervals on the evaluated spectrum, thus causing problems in selection of the spectrum peak.

The signal analysis unit 12 previously performs, when setting the model order, the simulation utilizing the signal model including the ideal peak component, especially the ideal heartbeat signal model in the embodiment of the present invention. The description will be given below of the process of deriving the maximum value of the model order and the optimum value of the model order, which are obtained by the simulation. The model proposed by Mr. D. R. Morgan and Mr. M. G. Zierdt is applied as the above-mentioned ideal heartbeat model (see FIG. 3).

The simulation process utilizing the signal model including the ideal peak component (the ideal heartbeat signal model) includes a step of setting the signal model in a plurality of patterns having the respective different peak frequencies, by setting the frequency of the peak component (the heartbeat frequency) in the signal model, which has a time window at a predetermined time and includes the ideal peak component (the ideal heartbeat signal model), while shifting it by a predetermined frequency within the range corresponding to the frequency bandwidth of the peak component to be measured, which is actually applicable. In addition, there are set a plurality of analysis durations for which the spectrum estimation is to be applied, while making its period of time different from each other by a predetermined time within the above-mentioned time window.

More specifically, in case of the heartbeat to be measured, there is set a total of 48 patterns of the heart-signal models, which become the respective different peak frequencies, by setting the heartbeat frequency in the ideal heartbeat signal model having the time window of for example 5 seconds, while shifting it by 0.0167 Hz (corresponding to the heartbeat 1 cycle/min) within the range of frequency from 0.7 Hz to 1.5 Hz, between which the heartbeat of a human at rest in a sitting posture actually exists. In addition, there is set a total of 49 patterns of the analysis durations from 0.1 seconds to 5 seconds, by making it different from each other by 0.1 seconds within the time window (5 seconds).

Successively, the respective spectrum estimation is made with the above-mentioned analysis data point number used as the maximum value of the model order, in each combination of the respective signal model and the respective analysis duration, while changing the model order from 1 to the maximum value as mentioned above, and there is made a detection of an existence of the spectrum peak within the range corresponding to the frequency bandwidth of the peak component to be measured (the heartbeat frequency), which is actually applicable, and when the spectrum peak exists, its model order is estimated as the effective model order.

More specifically, in case of the heartbeat, there is performed the spectrum estimation for each of the combinations of the respective heartbeat signal model and the respective analysis durations (48×49=2352 patterns), while changing the model order from 1 to the maximum value as mentioned above, there is made a detection of an existence of the spectrum peak for the respective model order within the range of from 0.7 to 1.5 Hz within which the heartbeat frequency may actually exist (see FIG. 11), and when the spectrum peak exists, its model order is estimated as the effective model order. The analysis data point number is a product of the analysis duration and the predetermined sampling frequency. In case of the heartbeat to be measured, the value of the sampling frequency (1000 Hz) of the signal as actually measured may be selected for example.

Then, the minimum value of the effective model orders in the respective combination of each the signal model and each the analysis duration is extracted in the thus obtained effective model orders, and the largest of the minimum values of the model order is used as the minimum value of the model order. The spectrum estimation can be surely conducted by setting the model order used in the spectrum estimation relative to the actual phase difference signal within the range of from the thus obtained minimum value to the maximum value of the analysis data point number as mentioned above.

In a specific example of the heartbeat, the minimum value of the effective model orders in the respective combination (2352 patterns) of each the signal model and each the analysis duration is extracted in the effective model orders as obtained. For example, in the signal model of 0.7 Hz of the heartbeat frequency, no spectrum peak exists under about 700 of the model order and it is not the effective model order, with the result that the minimum value of the model order is about 700. In the similar manner, in the signal model of 1.1 Hz of the heartbeat frequency, the minimum value of the model order is about 350 and in the signal model of 1.5 Hz of the heartbeat frequency, the minimum value of the model order is about 300 (see FIGS. 5 and 6). Concerning the largest of the minimum values of this model order, in this example, the largest is about 700 (see FIG. 4), which is the smallest model order in the case of the heartbeat frequency of 0.7 Hz, this is used as the minimum value of the model order. In view of the state that no spectrum peak may exist in the spectrum estimation in case of the heartbeat frequency of at least 0.7 Hz, the use of the smallest value of about 700 or more of the model order in the actual spectrum estimation permits to perform surely the spectrum estimation even in any heartbeat frequency and any analysis duration.

Here, the frequency of the spectrum peak, which exists in response to the effective model order as previously estimated, is deemed as an estimated peak frequency of the effective model order. For the effective model order in the respective combination of each the signal model and each the analysis duration, there is calculated an amount of difference of the estimated peak frequency relative to the peak frequency of the corresponding signal model, i.e., an estimation error, and for the respective combination of each the signal model and each the analysis duration, there is extracted, as a representative model order, the model order, which has the estimated peak frequency in case where the above-mentioned estimation error becomes smallest (however, in case where a plurality of corresponding model orders exist, the smallest value of them).

The respective representative model orders are compiled for the same analysis duration and averaged, and an averaged value for the respective analysis duration is obtained as an averaged model order. The averaged model orders are plotted in a graph by locating the analysis duration on the abscissa and the value of the model order on the ordinate (see FIG. 8), and the value of the model order, which forms the most approximate straight line to a line caused by the plotting, is estimated as the optimum value of the model order. The use of this optimum value in the actual analysis permits to make the difference between the frequency of the spectrum peak as obtained and the frequency of the peak component to be actually measured small in any heartbeat frequency and any analysis duration, thus obtaining desired estimation results.

Figure 4:
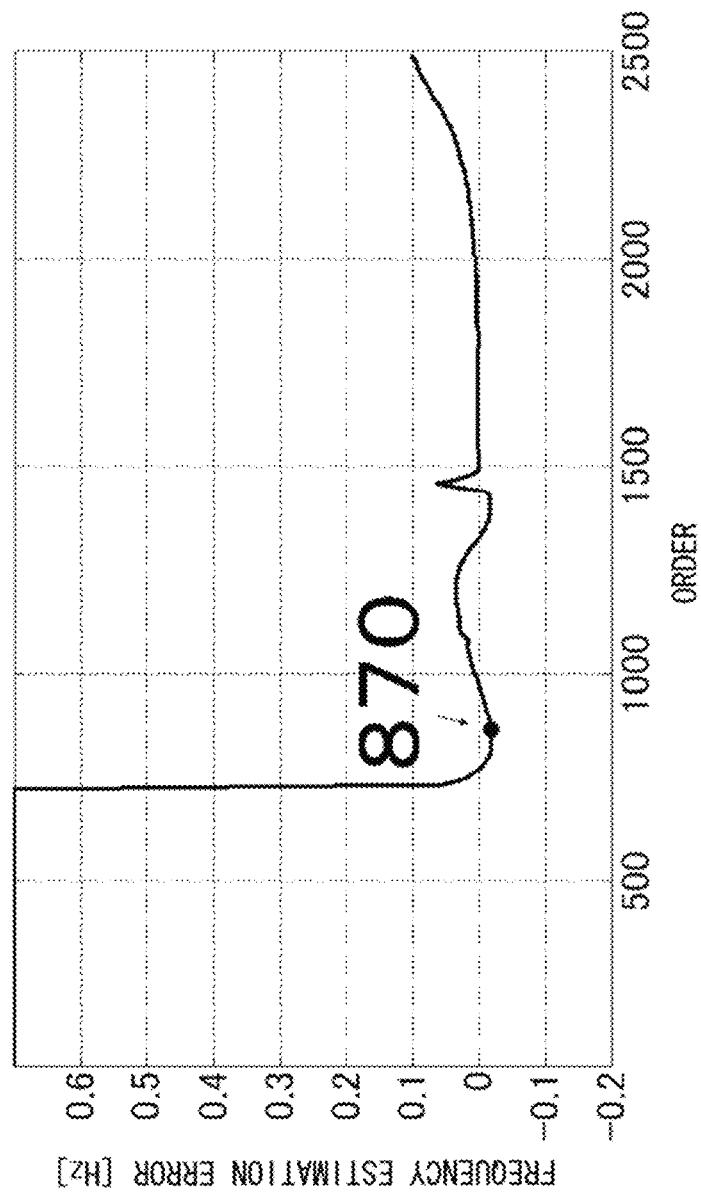
FIG. 4 is a graph showing a relationship between a model order and an estimation error in case where the signal model has a heartbeat frequency of 0.7 Hz in a simulation in the system according to the embodiment of the present invention for measuring a peak frequency of a signal.
Figure 5:
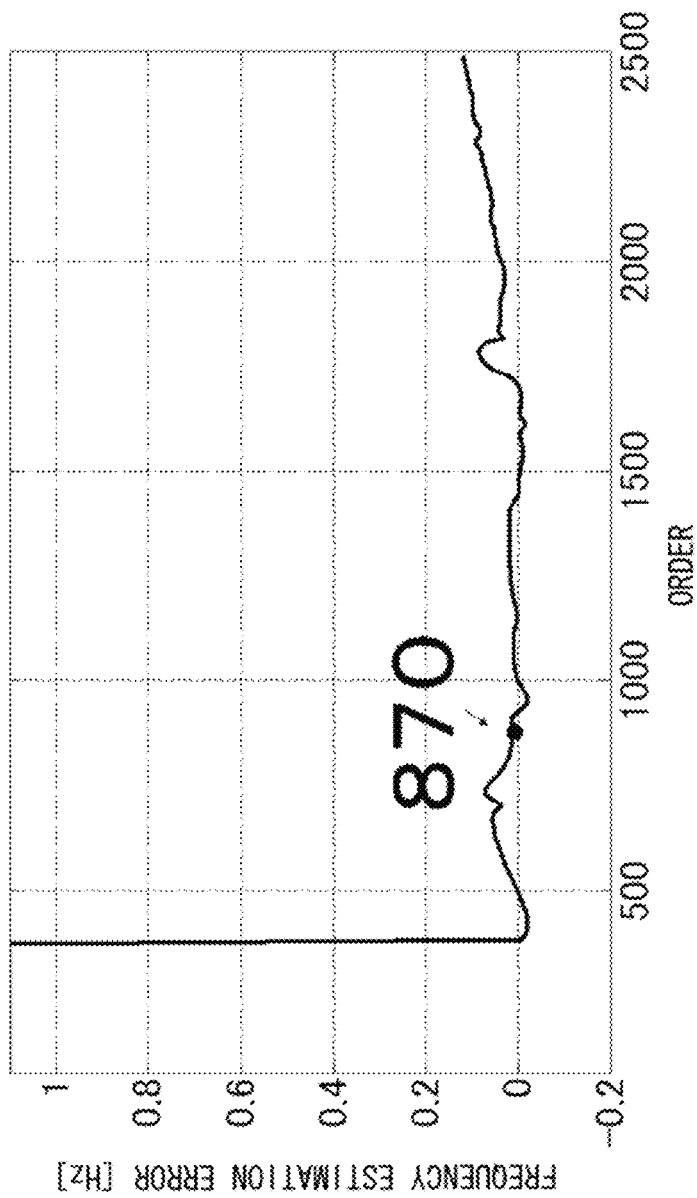
FIG. 5 is a graph showing a relationship between a model order and an estimation error in case where the signal model has a heartbeat frequency of 1.1 Hz in a simulation in the system according to the embodiment of the present invention for measuring a peak frequency of a signal.
Figure 6:
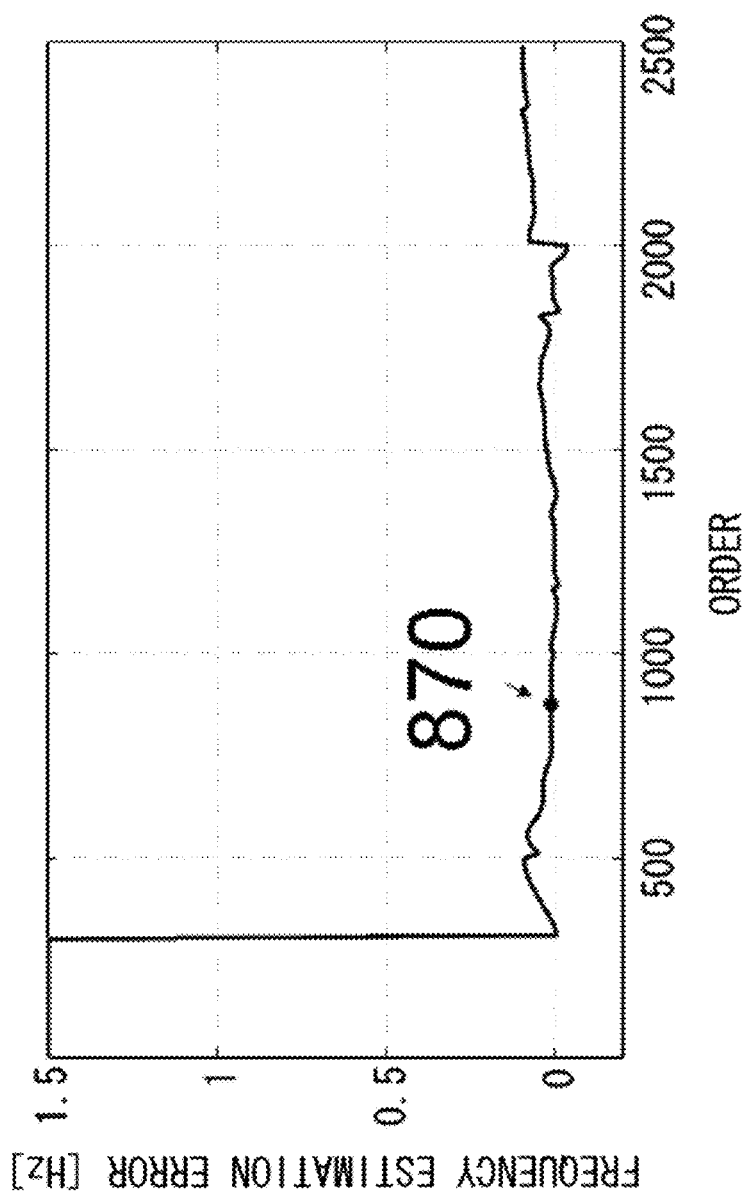
FIG. 6 is a graph showing a relationship between a model order and an estimation error in case where the signal model has a heartbeat frequency of 1.5 Hz in a simulation in the system according to the embodiment of the present invention for measuring a peak frequency of a signal.
Figure 7:
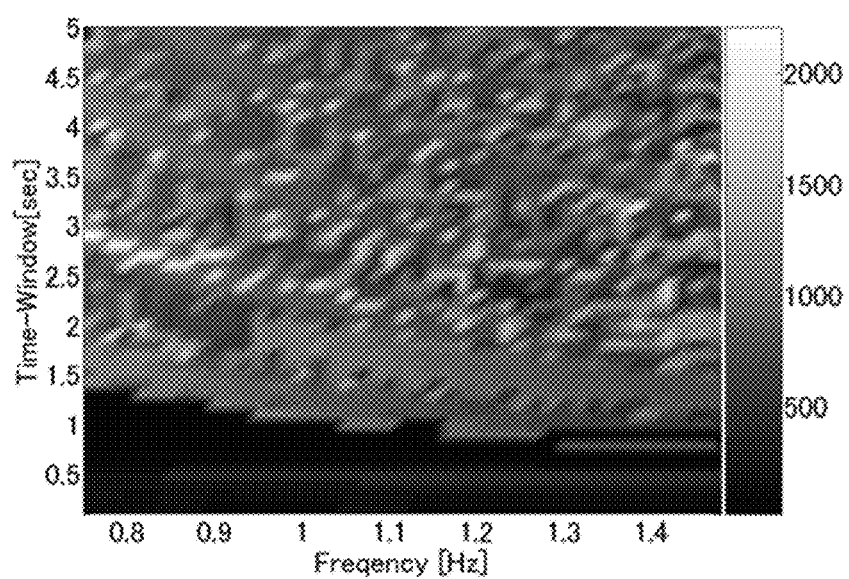
FIG. 7 is a spectrum diagram showing a relationship between a heartbeat frequency, an analysis duration and a representative model order, which are obtained through a simulation in the system according to the embodiment of the present invention for measuring a peak frequency of a signal.

In a specific example of the heartbeat, there is obtained the estimation error for the effective model order in the respective combination of each the signal model and each the analysis duration, and the representative model order is extracted in the effective model order in the respective combination of each the signal model and each the analysis duration. FIG. 4 shows a relationship between the model order and the estimation error in case where the signal model has a heartbeat frequency of 0.7 Hz. FIG. 5 shows the relationship in case where the signal model has a heartbeat frequency of 1.1 Hz, and FIG. 6, the relationship in case where the signal model has a heartbeat frequency of 1.5 Hz. However, in FIGS. 4 to 6, for the model order in which no spectrum peak exists, the value of the heartbeat frequency itself is indicated as the error. FIG. 7 shows a relationship between various kinds of heartbeat frequencies, analysis durations and representative model orders. In this figure, although magnitude of the model order is indicated by light and dark, the lower and dark portion (black portion) in FIG. 7 indicates no existence of the spectrum peak in any model order.

Figure 8:
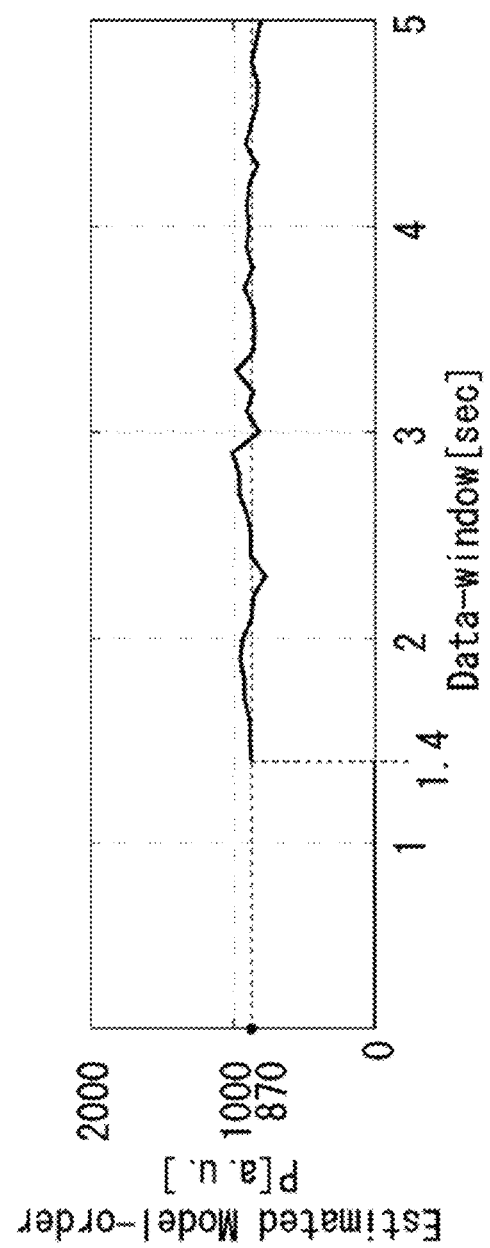
FIG. 8 is a graph showing a relationship between an averaged model order and an analysis duration, which are obtained through a simulation in the system according to the embodiment of the present invention for measuring a peak frequency of a signal.

When, in case of the heartbeat, the averaged model orders in which the respective model orders have been averaged for the same analysis duration, are plotted in a graph by locating the analysis duration on the abscissa and the value of the model order on the ordinate, the value of the model order, which forms the most approximate straight line to the line caused by the plotting, is about 870 as shown in FIG. 8. It is preferable to utilize it as the optimum value of the model order in the spectrum estimation.

In addition, the signal analysis unit 12 is required to estimate previously the appropriate analysis duration, together with the model order in the spectrum estimation as mentioned above. The signal analysis unit estimates, as the effective model order, the model order in case where the spectrum peak exists in the above-described simulation utilizing the signal model (the ideal heartbeat signal model) including the ideal peak component upon setting the model order. However, there may be a case where no spectrum peak has existed and any effective model order has not been set, due to unsuitable conditions of the analysis duration. Therefore, the value of the analysis duration, which has the longest analysis duration in the respective combination of each the signal models for which any effective model order has not been set and each the analysis durations, is deemed as a boundary value in the above-mentioned simulation, and the analysis duration, which is larger than this boundary value, is set as the effective value. The analysis duration as set so as to be larger than the above-mentioned boundary value permits to prevent a case where any spectrum peak does not exists in the spectrum estimation from being caused, thus performing the spectrum estimation.

In the specific case of the heartbeat, the spectrum estimation is made for each of the combinations of the respective heartbeat signal model and the respective analysis durations (48×49=2352 patterns), while changing the model order from 1 to the maximum value as mentioned above, there is made a detection of an existence of the spectrum peak for the respective model order within the range of from 0.7 to 1.5 Hz within which the heartbeat frequency may actually exist, and when the spectrum peak exists, its model order is estimated as the effective model order in the same manner as the model order as described above. In addition, the value of the analysis duration, which has the longest analysis duration in the respective combination of each the signal models for which any effective model order has not been set and each the analysis durations, i.e., the analysis duration of about 1.3 seconds in case of the heartbeat frequency of 0.7 Hz is deemed as the boundary value, and the analysis duration, which is larger than this boundary value, i.e., the analysis duration of at least 1.4 seconds is set as the effective value.

In addition, the signal analysis unit 12 obtains, in case of the heartbeat to be measured, a value of LF/HF, while changing the value of the analysis duration, in order to previously set the analysis duration, which can be appropriately used, and calculates an evaluation accuracy (a normalized error rate) of the stress evaluation value LF/HF in comparison with the reference value of LF/HF based on the measurement utilizing the electrocardiograph in an independent manner, and extracts the range of the analysis duration in which the error rate is small, thus carrying out these steps.

More specifically, a relationship between the analysis duration and the evaluation accuracy of LF/HF is investigated utilizing the actual measurement data of five heartbeat signals as measured for a period of time of 180 seconds by receiving the microwave at rest in a sitting posture. First, the heart rate variability (HRV) is caused to be reproduced from the actual measurement data as mentioned above, while increasing the analysis duration by 0.1 seconds within a range of from 1.4 seconds to 5 seconds. The value of LF/HF for each the analysis duration is obtained from the reproduced HRV is obtained, and the normalized error rate is calculated from the thus obtained value and the value of LF/HF obtained based on the heartbeat measurement utilizing the electrocardiograph in an independent manner under the same measurement conditions. This normalized error rate may be calculated as follows:

Error rate=|(LF/HF through electrocardiograph)−(LF/HF through microwave measurement)|/(LF/HF through electrocardiograph)

Figure 9:
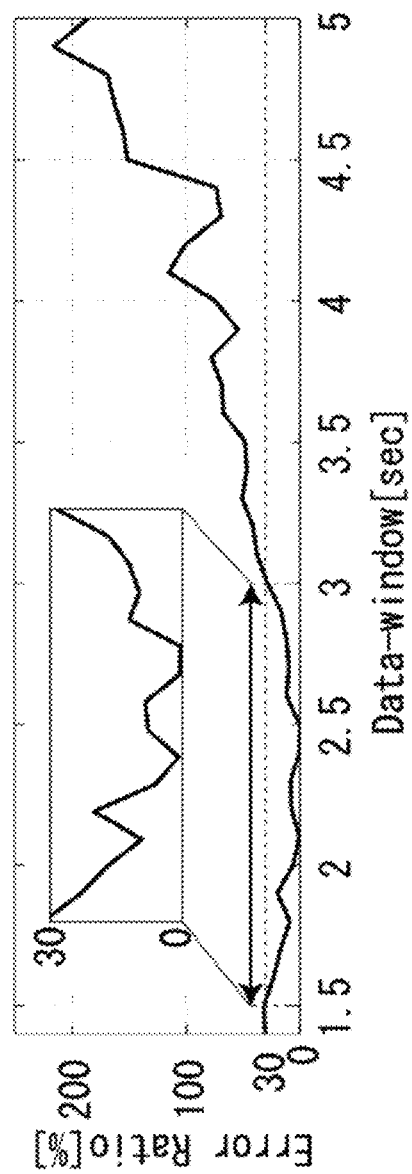
FIG. 9 is a graph showing a relationship between an analysis duration and an error rate from an LF/HF value obtained through the system according to the embodiment of the present invention for measuring a peak frequency of a signal relative to an LF/HF value from an electrocardiograph.

The minimum value of the error rate as obtained is normalized as "0" to resolve dispersion of the error rate due to the measurement accuracy of the heartbeat signal for the respective measurement data. There is calculated an average value between the actual measurement data of the normalized error data of LF/HF for the value of the respective analysis duration, as obtained for each of the five measurement data in this manner. When the analysis duration is within the range of from 1.5 to 3.0 seconds as shown in FIG. 9, the error rate becomes less than 30%. The dispersion of the error rate according to a personal difference is normally about 30%. Therefore, the variation of LF/HF in accordance with the state of variation for each individual is within the range of from 1.5 seconds to 3.0 seconds of the analysis duration, thus leading to a reproduction at a high accuracy.

In addition, the time in which the error rate is smallest within the range of from 1.5 seconds to 3.0 seconds of the analysis duration may be deemed as the optimum value, and this corresponds for example to the analysis duration of 2.5 seconds (see FIG. 9). It is therefore preferable to select this analysis duration of 2.5 seconds as the optimum value for the use of the actual analysis.

With the analysis duration as selected being long beyond necessity, stability (reliability) of the frequency estimation increases, however, time response for the heartbeat interval becomes dull in the reproduced variation of the heartbeat interval (HRV). More specifically, the variation of the heartbeat interval is smoothed. In case where, of the HRV, the variation of the frequency band (0.03 to 0.45 Hz) associated with the stress assessment is smoothed, there may be a possibility of creating adverse effects on the estimation of the stress assessment value LF/HF.

In addition, the signal analysis unit 12 is also required to set previously a shifted time to conduct repeatedly a set of steps for obtaining the frequency of the heartbeat with the MEM, while shifting the analysis range with the analysis duration in each analysis.

More specifically, in case of the heartbeat to be measured, for the frequency bandwidth (0.03 Hz to 0.45 Hz), which is required for the stress assessment utilizing the spectrum analysis of the variation of the heartbeat interval (HRV), the sampling frequency, which is required for reproducing the variation of this frequency bandwidth (0.03 Hz to 0.45 Hz) in the sampling process in the analysis, is higher than twice as the maximum frequency (0.45 Hz) in the bandwidth according to a sampling theory, namely the frequency higher than 0.9 Hz. Therefore, the signal analysis unit 12 therefore sets the shifted time, which is the reciprocal of the sampling frequency, as the time, which is obtained as the reciprocal of the frequency higher than the minimum value (0.9 Hz) of the sampling frequency, i.e., as the period of time being less than 1.1 seconds and longest as much as possible. This permits to set the shifted time as 1 second so that the sampling frequency becomes 1 Hz.

With the shifted time being short, the variation in time of the heartbeat frequency and the variation of the heartbeat interval (HRV) can be closely reproduced. However, the number of calculating processes increases, and time lags caused by each process are aggregated, thus causing a problem in difficulty of making a measurement in real time. On the other hand, with the shifted time being excessively long, the sampling frequency may not have an appropriate value, thus causing a problem in difficulty of capturing the variation of the frequency bandwidth (0.03 to 0.45 Hz) associated with the stress assessment in the HRV. This may create adverse effects on the estimation of the stress assessment value LF/HF.

In case of the heartbeat to be measured, the signal analysis unit 12 conducts repeatedly a set of steps for obtaining the frequency of the heartbeat of estimating the model order as 870, making the spectrum estimation with the analysis duration of 2.5 seconds in accordance with the MEM, detecting the value of the frequency of the spectrum peak within the range of from 0.7 Hz to 1.5 Hz, which is the range of the frequency of the heartbeat of a human at rest in a sitting posture, and using the resultant as the frequency of the heartbeat, while shifting, in each spectrum estimation, sequentially the analysis range for the phase difference signal by the shifted time of 1 second in the direction of a passage of time. It is therefore possible to obtain the frequency with the duration of the shifted time along the time axis of the phase difference signal at a high accuracy. The heartbeat frequency as successively obtained permits to capture the time variation of the heartbeat frequency.

The conversion unit 13 converts the frequency of the peak component of the signal as obtained by the signal analysis unit 12 into data of time by taking the reciprocal of this frequency and derives the occurrence time interval of the peak component to be measured. It is possible to obtain the variation of interval of the peak component, i.e., the heart rate variability (HRV) by repeating the derivation of the interval of the peak component. A transition with time of the frequency may be obtained from the thus obtained heart rate variability through Wavelet conversion, etc., permitting to use it in the stress assessment.

The calculation section 11h of the electromagnetic wave transmitting and receiving unit 11 as described above, the signal analysis unit 12 and the conversion unit 13 constitute a computer provided with a CPU, a memory, output and input interfaces, etc., as the hardware structures of the computer so as to cause the computer to function as the above-mentioned calculation section 11h, the signal analysis unit 12 and the conversion unit 13 based on a program stored in the memory, etc. The results of measurement and calculation of the phase difference signal obtained by the calculation section 11h, the frequency (heartbeat frequency of the peak component to be measured, as obtained by the signal analysis unit 12, etc. are recorded and stored in the memory, etc. of the above-mentioned computer upon each measurement. The calculation section 11h, the signal analysis unit 12 and the conversion unit 13 as described above may constitute alone independently or in combination a plurality of computers. Such a computer may be constituted as a microcomputer in which a CPU, a Memory, a ROM, etc. are integrally provided.

Now, the description will be given of a state of use of the system according to the embodiment of the present invention for measuring a peak frequency of a signal. There is the assumption that a person (a human subject) serving as the subject 70 is placed at rest in a sitting posture, with the heartbeat frequency kept within the range of 0.7 Hz to 1.5 Hz (heart-rate: 42 to 90 per minute) so as to position a predetermined part of the human body in the vicinity of an antenna 11a in a state in which external oscillation may be applied to the subject 70. The electromagnetic wave transmitting and receiving unit 11 irradiates a continuous microwave from the antenna 11a to the subject 70 for a desired period of time of measurement, and receives a reflected wave from the subject 70 and outputs a phase difference signal between the irradiation wave and the reflected wave to the signal analysis unit 12.

The signal analysis unit 12 performs the spectrum estimation for the phase difference signal as obtained, with the use of the MEM with the analysis duration (2.5 seconds) as previously set, and derives, as the frequency of the heartbeat, the value of the frequency of the spectrum peak within the range of from 0.7 Hz to 1.5 Hz corresponding to the frequency bandwidth, in which the heartbeat at rest in a sitting posture actually exists, of the frequency power spectrum as estimated. Successively, the signal analysis unit newly set the analysis range with the analysis duration for the phase difference signal, by shifting the start point behind by the shifted time (1 second) as previously set, performs the spectrum estimation in the same manner and obtain the frequency of the heartbeat. Then, it conduct repeatedly a set of steps, while shifting, in each spectrum estimation, sequentially the analysis range with the analysis duration by the shifted time in the direction of a passage of time of the phase difference signal, and obtains the frequency for intervals of the shifted time along the time axis of the phase difference signal.

The conversion unit 13 converts, on each derivation of the frequency of the heartbeat by the signal analysis unit 12, the frequency into the data of time by taking the reciprocal of this frequency, to derive the heartbeat interval. Such successive obtainment of the heartbeat interval permits to obtain the heart rate variability (HRV).

When the heartbeat interval variation is successively frequency-analyzed in a state in which the heartbeat interval may successively be derived and handled as the heart rate variability (HRV), and especially it may be obtained in the form in which the time/frequency spectrum of the HRV may be indicated through Wavelet conversion, the time variation of the respective spectrum peak in the bandwidth of from about 0.03 Hz to 0.15 Hz (LF component) and the bandwidth of from 0.15 Hz to about 0.45 Hz (HF component) may be visibly recognized in a relatively short period of time. Application of this matter to the stress assessment makes it possible to judge a time zone in which the peak of the LF appears strongly than the HF as a state in which stress is applied to the human body, and judge a time zone in which the peak of the HF appears strongly than the LF as a relaxed state of the human body, thus making stress assessment in a short period of time.

In this case, it is possible to detect and assess the heartbeat interval without making a direct contact with the subject and putting him/her under constraint, to capture surely the heartbeat interval variation with free restraint applied to the subject, thus making appropriately a stress assessment and improving the assessment accuracy, unlike a conventional stress assessment method in which a time variation of the heartbeat interval, which has been read out from the peak interval of R-R of an electrocardiograph is frequency-analyzed, and a peak value LF of the low frequency component and a peak value HF of the high frequency component are used to obtain a value of LF/HF as a stress assessment value.

The values of the analysis duration relative to the phase difference signal, the analysis range for searching the spectrum peak in the frequency power spectrum, etc., correspond to those of the subject who is placed at rest in a sitting posture, with the heart-rate kept within the range of 42 to 90 per minute. These values may be appropriately changeable based on a state of the subject.

Concerning an application example of the system according to the embodiment of the present invention for measuring the peak frequency of the signal for analyzing condition of the subject, there may be available a system in which the antenna 11a of the electromagnetic wave transmitting and receiving unit 11 is placed as a monitor for a health condition in a place where a person to be measured leads a daily life or a predetermined place in a hospital room, for example in the vicinity of a bed, a state variation of a so-called vital signs such as heartbeat, respiratory rate of a human during a physical activity or during sleep, etc., to make assessment in stability of the health condition, etc. In case of making a stress assessment, there may be available a system in which the antenna 11a of the electromagnetic wave transmitting and receiving unit 11 is embedded in a driving seat of an automobile and the heartbeat interval variation is derived without putting a driver under constraint, and the stress assessment while driving is made substantially without delay from an actual time, thus providing the driver with indexes for taking a break or having time for rest, or with a warning about falling asleep at the wheel.

In addition to the foregoing, the present invention may be applied to a device-monitoring system in which the antenna 11a of the electromagnetic wave transmitting and receiving unit 11 is placed in a health-related device for domestic use, the heartbeat interval variation of a user is obtained along with an operation of the device and a stress state of the user during use of the device is assessed substantially without delay from an actual time, so that, when a state of stress is considered as being appearing, an intensity of the device is decreased. It may also applied to a stress analysis system in which the antenna 11a of the electromagnetic wave transmitting and receiving unit 11 is placed in an working atmosphere of an operator, the heartbeat interval variation is derived without putting an operator under constraint to make a stress assessment during operation, a further assessment about degree of fatigue is made based on a state of stress during operation, and the resultant data may be used as a guideline relative to compatibility of the operator with the operation, or as an index relating to a period of time for rest, etc.

According to the system of the embodiment of the present invention for measuring a peak frequency of a signal for analyzing condition of a subject, the signal analysis unit executes the spectrum estimation utilizing the Maximum Entropy Method for a part of the phase difference signal, which is obtained by the electromagnetic wave transmitting and receiving unit 11, and may include peak components to be measured and noises, which are not to be done, with a predetermined short analysis duration, to obtain the frequency indicative of the occurrence frequency of the peak component, from the above-mentioned phase difference signal, and conducts repeatedly the process of calculating the frequency on a time axis of the phase difference signal, while shifting a position to be measured by the shifted time, corresponding to an analysis duration, thus introducing continuously the frequency. It is therefore possible to know the frequency of the peak component and a transition with time of the time interval of the peak component, which may be obtained as the reciprocal of the frequency. As a result, it is possible to derive effectively a state of variation of the peak component to be measured, even in case where the signal obtained by the electromagnetic wave transmitting and receiving unit 11 includes a noise so that the peak component to be measured is not clearly revealed. In addition, for example, in case where the heartbeat is to be measured, it is possible to derive successively the frequency of the heartbeat and the heartbeat interval to obtain a heart rate variability (HRV) in a short period of time and a stress assessment, etc. utilizing this heart rate variability can also be made in a short period of time.

Figure 10:
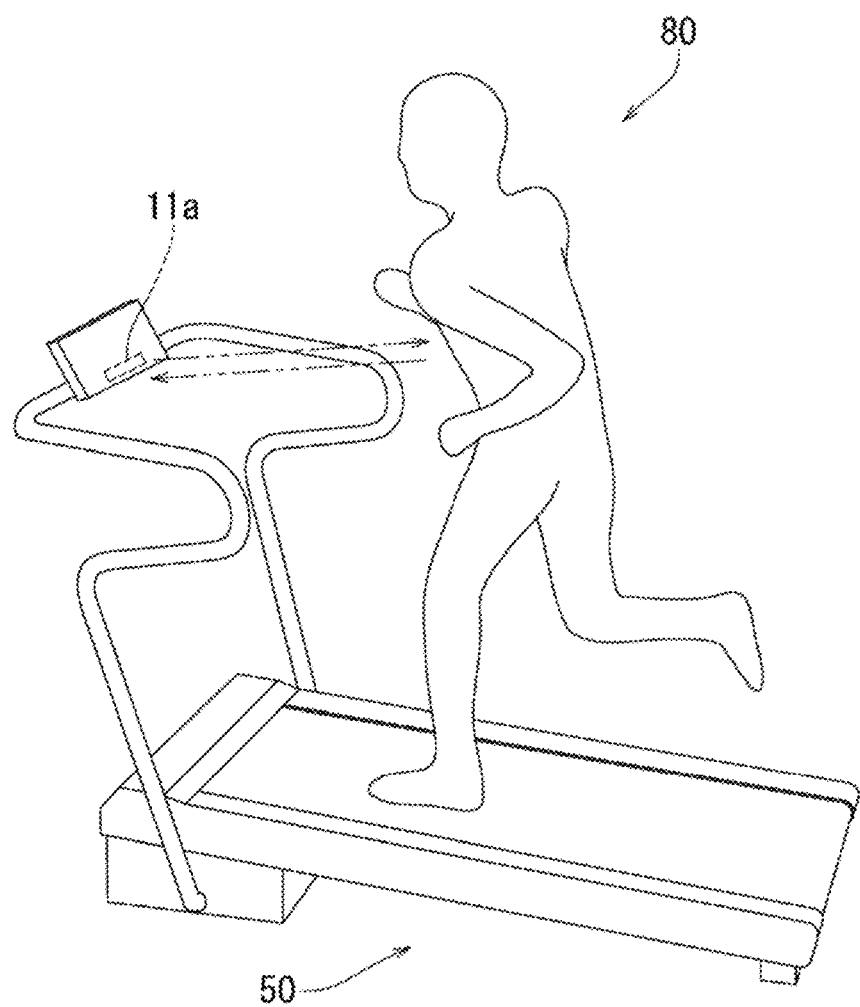
FIG. 10 is a descriptive view showing an example of applying the system according to the embodiment of the present invention for measuring a peak frequency of a signal to a heartbeat measurement relative to a person using a treadmill.

In addition to the monitoring of the health conditions as mentioned above, the system according to the embodiment of the present invention for measuring the peak frequency of the signal for analyzing condition of the subject may be applied to a measurement system of obtaining heartbeat of a person who is for example having a training for running on a treadmill, without making a contact with the person. In this case, it is preferable to place provide the antenna 11a of the electromagnetic wave transmitting and receiving unit 11 in the treadmill 50 (see FIG. 10). This antenna 11a irradiates the microwave, for example, to the chest of the person 80 as the subject during the training and receives the reflected wave from it, with the result that the phase difference signal including substantially the periodical peak component may be obtained and the frequency of the heartbeat may be obtained, and the heartbeat interval may be derived, thus permitting to calculate the number of heartbeat from this heartbeat interval. It is possible to measure the number of heartbeat from a separate place without making a direct contact with the person on the treadmill and cause the person himself or herself having the training or the other person such as an instructor to recognize the number of heartbeat as the measurement results substantially without delay, thus utilizing effectively these data as reference information such as pacing of the training. In addition, it is not necessary for the person having the training to attach a measurement device to the body unlike the conventional manner, continue the training without having a feeling of inconvenience of attaching the device and stress caused by attaching the device, thus making an intensive training.

Figure 11:
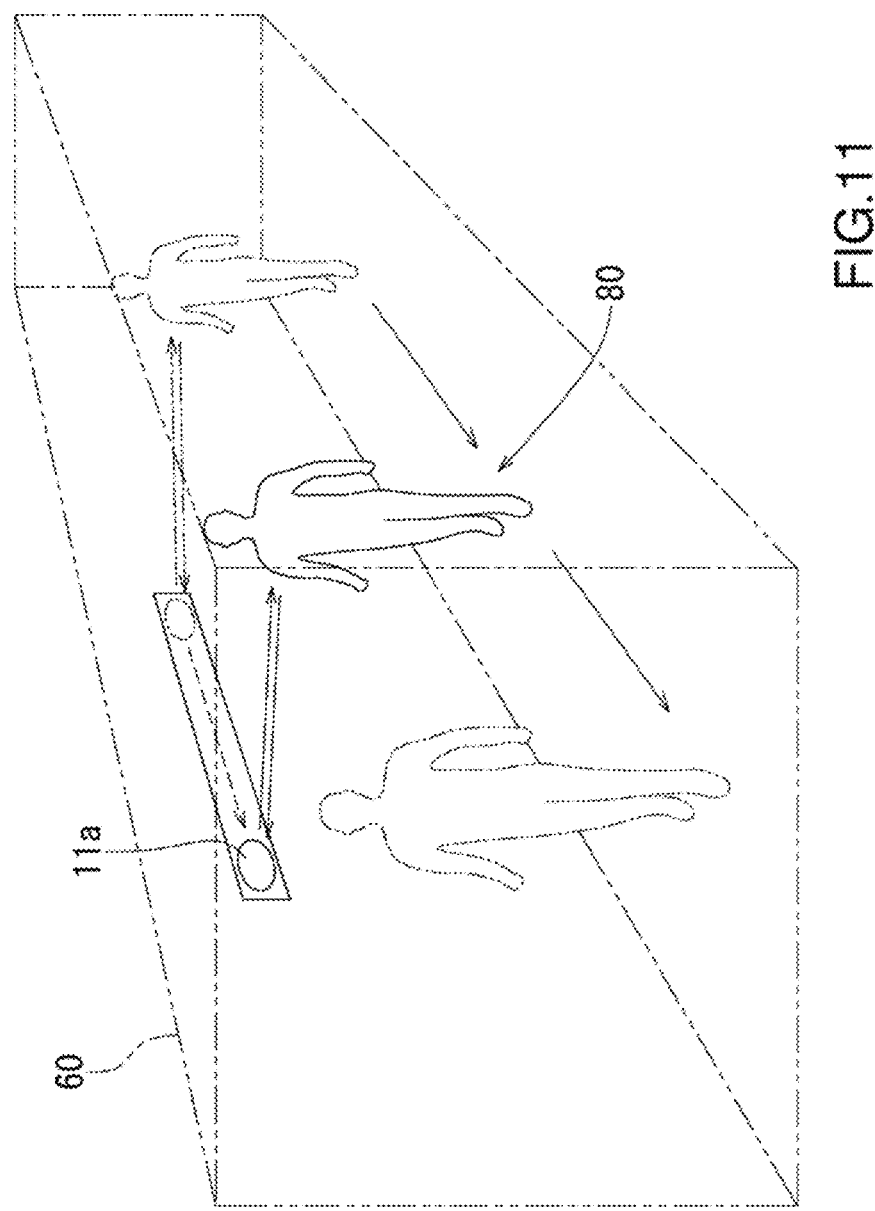
FIG. 11 is a descriptive view showing an example of applying the system according to the embodiment of the present invention for measuring a peak frequency of a signal to a heartbeat measurement and a stress assessment relative to a passer on a walkway.

In addition, the system according to the embodiment of the present invention for measuring the peak frequency of the signal for analyzing condition of the subject may be applied to a monitoring system in which the heartbeat interval of a person who passes through a predetermined area, and a stress assessment is made based on the heart rate variability to recognize a state of the person at a separate place without making a direct contact with him or her. In a walkway 60 through which a person who goes in and out for example an airport, etc., necessarily passes, as set as an area to be measured, as shown in FIG. 11, the antenna 11a of the electromagnetic wave transmitting and receiving unit is placed in the walkway 60 so as to be capable of making adjustment of orientation and/or a position of the antenna, in response to movement due to a passing action of the passer 80 on the walkway, the step of transmitting and receiving the microwave relative to the passer 80 on the walkway is continuously carried out for a predetermined period of time to derive the heartbeat interval and to calculate the number of heartbeat from the heartbeat interval, and obtain the heart rate variability where appropriate, so as to make a stress assessment, thus permitting to monitor a state of the person without causing the passer 80 to be aware of measurement. This permits to recognize an abnormal condition in which the person has the different number of heartbeat from a normal condition, thus making it possible to pay rapid attention to possibility of disease, which has influence on the heartbeat, and especially affected infection, thus utilizing them as countermeasure against the infection. In view of the fact that a stress estimation permits recognition of a person who is placed under a stress condition, concerning a security countermeasure against a terrorist who has an external appearance, which is not distinguishable from a normal person, it is possible to recognize the slightest sign of a stress, based on the matter that a terrorist is expected to be placed under a stress condition due to a terrorist plan or a terrorist action, to detect a person suspected to be a terrorist, thus having a connection to appropriate measures by security authorities, etc.

In addition, it is possible to provide, as the other application example of the system according to the embodiment of the present invention for measuring the peak frequency of the signal for analyzing condition of the subject, an apparatus which is provided integrally with the whole system having a reduce size so as to be able to be held by a hand, and has a configuration of irradiating a microwave from the handheld-type apparatus relative to a person who is running in sport (e.g., a marathon), etc., receiving a reflected wave from it, and measuring the heartbeat to obtain information on the number of heartbeat, etc. In this case, it is possible for a measurer who holds the apparatus in his/her hand to perform an appropriate measurement by moving the antenna of the apparatus in response to his/her motion so as to direct it to him/her.

The system according to the embodiment of the present invention for measuring the peak frequency of the signal for analyzing condition of the subject is described as having a configuration that the heartbeat frequency obtained by the signal analysis unit 12 is converted into the heartbeat in the form of reciprocal thereof by the conversion unit 13, such a heartbeat is successively derived to obtain the heart rate variability (HRV), which is subsequently utilized for an assessment, etc. However, the present invention is not limited only to such a configuration. More specifically, there may be adopted a configuration of deriving successively the heartbeat frequency without using the conversion unit to obtain a time variation of the heartbeat frequency, which is subsequently utilized for an assessment, etc.

The system according to the embodiment of the present invention for measuring the peak frequency of the signal for analyzing condition of the subject is described as having a configuration that the phase difference signal obtained by the electromagnetic wave transmitting and receiving unit 11 is subjected to the process performed by the signal analysis unit 12 without performing any additional process. However, the present invention is not limited only to such a configuration. More specifically, there may be adopted a configuration of sending the phase difference signal as obtained to a predetermined filtering process unit to attenuate unwanted components and then subjecting the resultant to the process by the signal analysis unit 12. This permits to make the treatment of the spectrum estimation utilizing the MEM easy to reduce a treatment load, and perform for effectively the process between the step obtaining the phase difference signal and the step of obtaining the frequency of the peak component with the predetermined analysis duration of this phase difference signal.

In addition, the system according to the embodiment of the present invention for measuring the peak frequency of the signal for analyzing condition of the subject is described as having a configuration that the heartbeat is set as what is to be measured, the microwave is irradiated so that the phase difference signal includes substantially the periodical peak component of the heartbeat, and the spectrum estimation utilizing the MEM is repeated to obtain successively the frequency of the heartbeat. However, the present invention is not limited only to such a configuration. More specifically, there may be adopted a configuration of setting a timing of breathing as what is to be measured, in place of the heartbeat. It is possible to obtain the frequency of the breathing through the spectrum estimation, and make a stress estimation based on the time variation of the frequency in the same manner as the heart-beat, in view of the facts that a human tends to breathe shallowly and rapidly under a state of stress, but deeply and slowly under a relaxed state, and the phase difference signal, which has been obtained by the electromagnetic wave transmitting and receiving unit through irradiation of the microwave to the subject may include an oscillatory wave component having a smaller amplitude and a higher frequency under a state of stress in response to the breathing, but having a larger amplitude and a lower frequency under a relaxed state in response thereto.

In addition, there may be adopted a configuration of setting, as what is to be measured, an up-and-down motion (blink) of an eyelid, which may occur as substantially the stationary variation in the same manner as the heart-beat, etc. Obtainment of the frequency of the up-and-down motion of the eyelid and/or the inter-blink interval is helpful for detection of falling asleep in view of the fact that the frequency of the motion of the eyelid tends to indicate the depth of sleep.

In addition, the system according to the embodiment of the present invention for measuring the peak frequency of the signal for analyzing condition of the subject is described as having a configuration that the variation of substantially the stationary heartbeat of a human serving as the subject is set as what is to be measured, the microwave is irradiated from the antenna 11a of the electromagnetic wave transmitting and receiving unit 11 to the human and the reflected wave from the human is received, so as to obtain the heartbeat frequency, the heartbeat interval and the number of heartbeat. However, the subject is not limited only to a biological body such as a human, an animal, etc. having substantially the stationary condition change as a so-called vital signs, but there may be adopted a configuration of handle, as the subject, for example, an internal combustion engine having substantially the stationary vibration corresponding to the number of rotation of an output shaft, an electric motor, an apparatus on which such an engine or motor is mounted, etc. It is possible to obtain, at a separate place, the frequency or the peak interval of the peak component, which is indicative of the condition change such as the vibration to be measured, from such an object in a state a possible external noise component may be applied, to make an appropriate assessment on the state of the object, even in a condition that a sensor may not be attached directly to the object.

The system according to the embodiment of the present invention for measuring the peak frequency of the signal for analyzing condition of the subject was used to verify as to whether or not the heartbeat frequency was obtained with a high accuracy through the spectrum estimation based on the conditions as set, and make assessment of examples in which the heartbeat is actually set as what is to be measured and variation of the heartbeat interval as derived was applied to stress assessment, in comparison with the heartbeat variation based on the heartbeat measurement by the electrocardiograph in comparison cases and stress assessment results obtained by utilizing it.

First, the spectrum estimation was made for the signal in which a white noise was added to the ideal heartbeat signal model, to verify as to whether or not application of the spectrum estimation according to the present invention, utilizing the MEM permitted to derive the heartbeat frequency with a high accuracy, even when the phase difference signal included the noise.

Initially, the model proposed by Mr. D. R. Morgan and Mr. M. G. Zierdt was applied as the ideal heartbeat model (see FIG. 3) to create a heartbeat signal having the heartbeat frequency of 1 Hz. The white noise was added to this ideal heartbeat signal so that an S/N of the signal became 3 dB.

Figure 12:
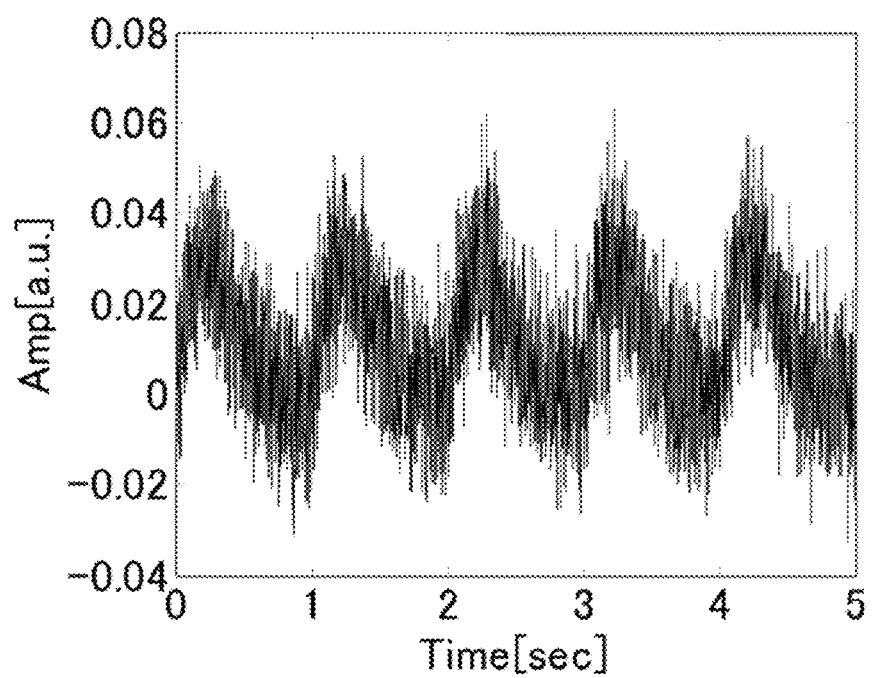
FIG. 12 is a graph showing a signal in which a white noise is applied to an ideal heartbeat signal used in the system according to the embodiment of the present invention for measuring a peak frequency of a signal.

FIG. 12 shows a graph of the signal, which was obtained by adding the white noise to the ideal heartbeat signal.

Figure 13:
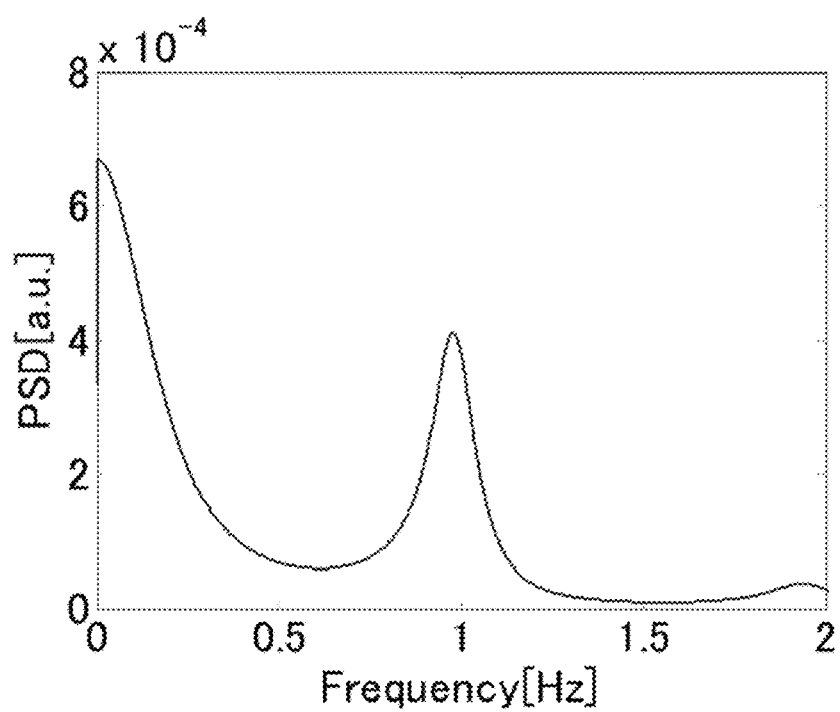
FIG. 13 is a power spectrum diagram obtained for a noise-applied signal used in the system according to the embodiment of the present invention for measuring a peak frequency of a signal.

This signal was used to derive the heartbeat frequency based on the spectrum estimation utilizing the MEM. The auto-regressive model order in the spectrum estimation was set as 870, and the analysis duration was set as 2 seconds therein. There was detected, in the power spectrum, a value of the frequency of the spectrum peak within the range of frequency of from 0.7 Hz to 1.5 Hz, between which the heartbeat at rest in a sitting posture actually exists, and the resultant value was used as the heartbeat frequency. FIG. 13 shows a power spectrum diagram obtained for the noise-applied signal in the spectrum estimation.

The heartbeat frequency as estimated was 0.98 Hz, and the difference of it from the heartbeat frequency (1 Hz) of the ideal heartbeat signal was 0.02 Hz, thus being an excessively small value as kept. No spurious peaks appeared within the range of from 0.7 Hz to 1.5 Hz.

It was revealed that the spectrum estimation utilizing the MEM by the signal analysis unit according to the present invention permitted to provide effective functions even when the S/N ratio of the signal was low, and namely the noise was large by making the conditions such as the model order, the analysis duration, etc., appropriate, thus deriving the heartbeat frequency with a high accuracy.

Then, the system according to the embodiment of the present invention for measuring the peak frequency of the signal for analyzing condition of the subject was used to obtain the phase difference signal including the peak component corresponding to the heartbeat, calculate the heartbeat frequency and to derive the variation of the heartbeat interval to make a stress assessment.

When obtaining the phase difference signal, the antenna of the electromagnetic wave transmitting and receiving unit was placed on a back side of the subject in a sitting posture so as to irradiate the microwave to the back of the subject, thus measuring a motion of the body surface in response to the beat of the heart.

The microwave generated by the microwave oscillator had a frequency of 10.525 GHz and an output of 10 dBm. The microwave was passed through the directional coupler and then attenuated by the attenuator having the attenuation characteristic of from 6 to 10 dB, and sent to the circulator, and then irradiated from the antenna.

The reflected wave from the subject was passed through the circulator, sent to the amplifier having the amplification characteristic of 40 dB and amplified, and then sent to the quadrature detector. The signal component based on the phase variation was obtained by the quadrature detector, and the resultant was processed by the calculation section, and then the phase difference signal including the peak component of the motion (oscillation) of the reflection surface corresponding to the heartbeat was outputted.

In addition, the measurement of the heartbeat was made by the electrocardiograph at the same time when the measurement by the microwave was made. Electrodes of the electrocardiograph were brought into direct contact with a plurality of parts of the body of the subject to make measurement in the same manner as a measurement by the electrocardiograph as commonly applied.

Both the measurement by the microwave and the measurement by the electrocardiograph were made under a condition that vibration caused by an engine was applied to the subject and the measurement system in a non-quiescent environment in an automobile, and the period of time of measurement was 900 seconds.

Figure 14:
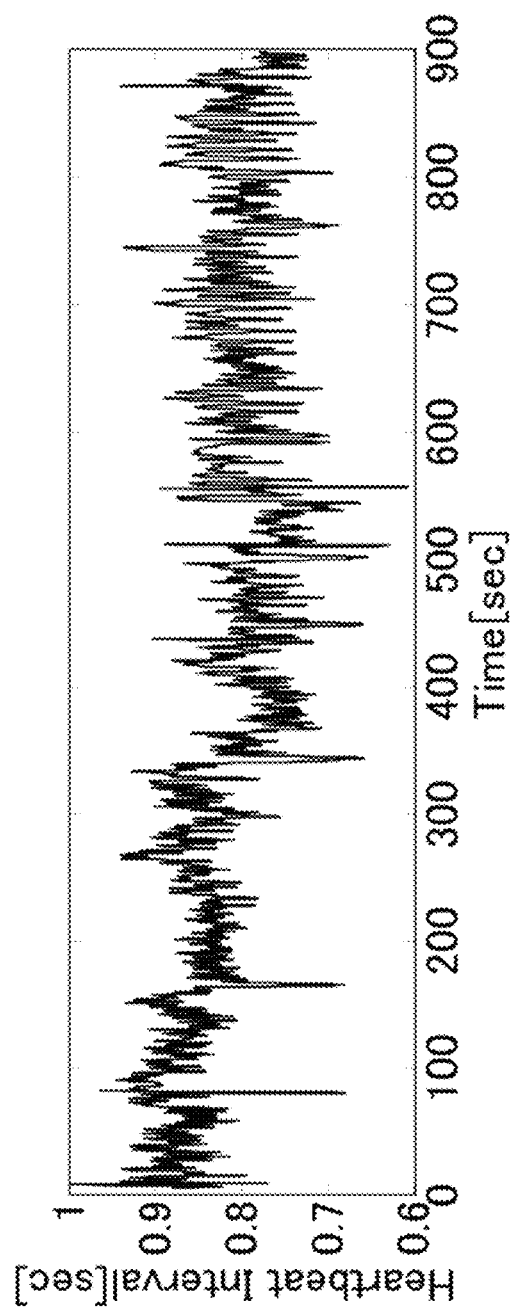
FIG. 14 is a graph of a heart rate variability (HRV) based on the heartbeat interval as extracted by the system according to the embodiment of the present invention for measuring a peak frequency of a signal.

The spectrum estimation utilizing the MEM by the signal analysis unit was repeatedly performed for the phase difference signal obtained by the electromagnetic wave transmitting and receiving unit, while shifting, in each spectrum estimation, sequentially the analysis range by the shifted time of 1 second from the start side of the phase difference signal toward the direction of a passage of time, thus deriving the frequency of the heartbeat at intervals of 1 second over the entire period of time of measurement. The heartbeat interval was obtained by converting into the time by the conversion unit by taking the reciprocal of the frequency, upon each derivation of the heartbeat frequency, and these steps were repeated to obtain the transition of time (variation) of the heartbeat interval, i.e., the HRV. FIG. 14 shows a graph in which the thus obtained HRV, namely the waveform of the heartbeat variation signal is plotted by locating the elapsed time (second) on the abscissa and the heartbeat interval (second) on the ordinate.

Figure 15:
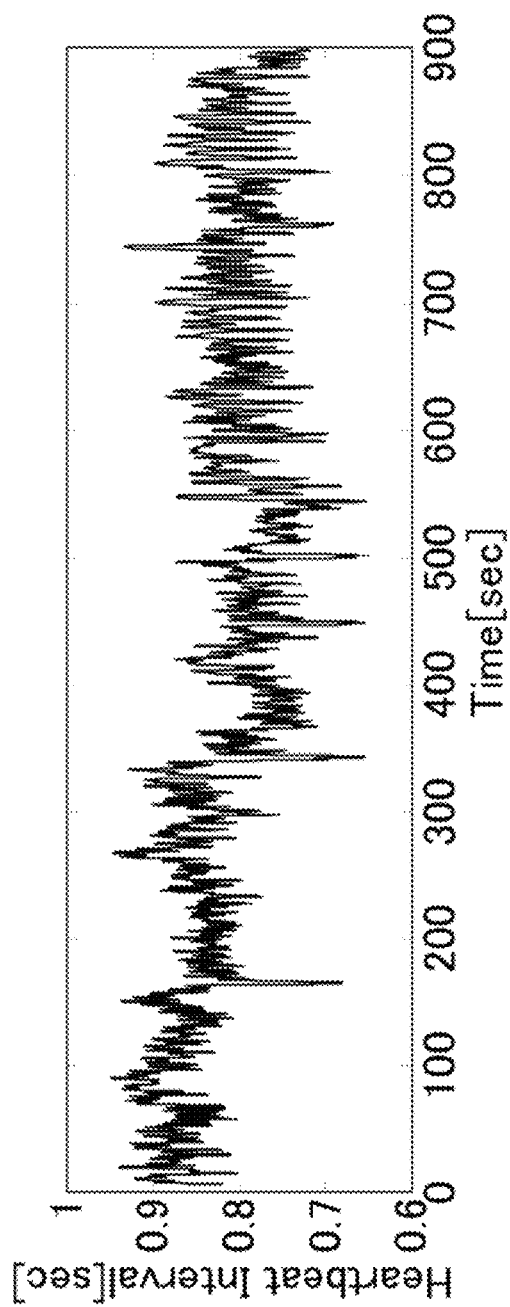
FIG. 15 is a graph of a heart rate variability (HRV) based on the heartbeat interval as obtained by an electrocardiograph of a comparison example relative to the embodiment of the present invention.

In addition, the heartbeat interval variation (HRV) was obtained from the signal wave in which the peak of the heartbeat obtained by the electrocardiograph appeared, as a comparison case. FIG. 15 shows a graph in which the thus obtained value is also plotted by locating the elapsed time (second) on the abscissa and the heartbeat interval (second) on the ordinate.

The HRV based on the measurement by the microwave as shown in FIG. 14 extremely approximated the HRV derived based on the peak corresponding to the heartbeat obtained by the electrocardiograph as shown in FIG. 15, thus revealing that the results obtained by the measurement by the microwave remarkably coincided with the result obtained by the electrocardiograph.

Figure 16:
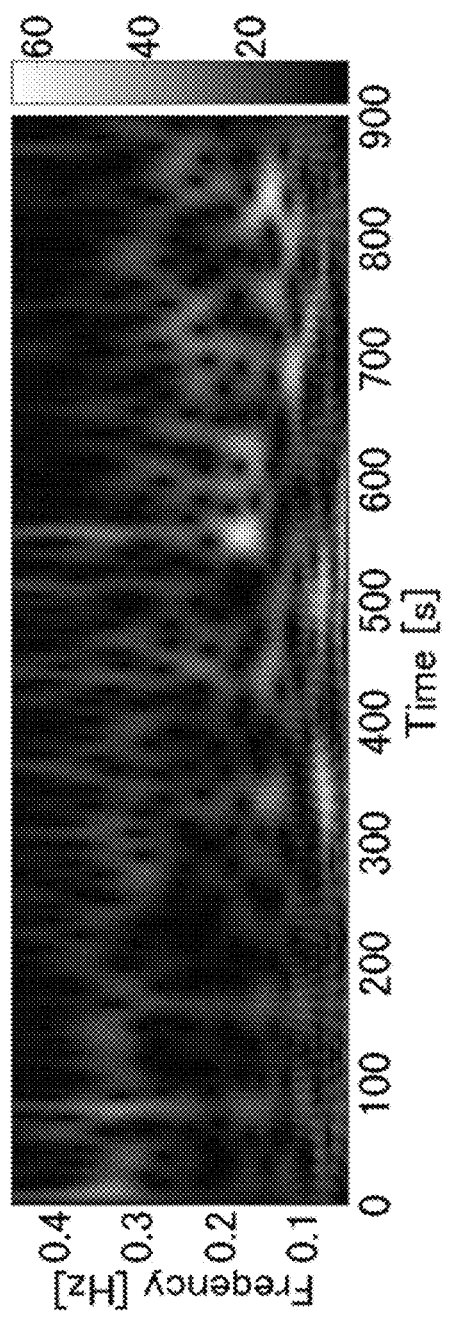
FIG. 16 is a spectrum diagram of Wavelet conversion results of a heartbeat variation obtained through the system according to the embodiment of the present invention for measuring a peak frequency of a signal.
Figure 17:
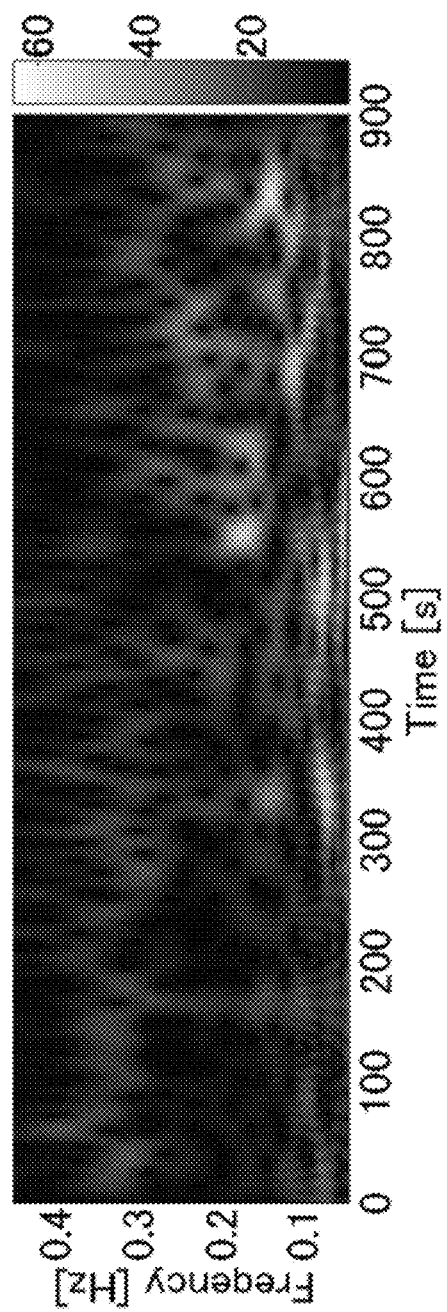
FIG. 17 is a spectrum diagram of Wavelet conversion results of a heartbeat variation from an electrocardiograph of a comparison example relative to the embodiment of the present invention.

In addition, the frequency-analysis based on Wavelet conversion was made for each waveform of the heartbeat interval variation (HRV) obtained through the measurement by the microwave and the analysis of the phase difference signal, and the heartbeat interval variation (HRV) obtained from the heartbeat peak interval obtained by the electrocardiograph in the comparison case. With the result of Wavelet conversion, the time/frequency spectrum of the HRV was indicated. There was recognized from the conversion results of spectrum the state in each frequency bandwidth, namely, variation with time of the peak value LF of the low frequency component (0.03 Hz to 0.15 Hz) and the peak value HF of the high frequency component (0.15 Hz to 0.45 Hz), serving as the stress assessment value. The results of Wavelet conversion in case of the measurement by the microwave were shown in FIG. 16 and those in case of the measurement by the electrocardiograph were shown in FIG. 17. The ordinate of the respective figure indicates the value of the frequency, and the abscissa thereof indicates time, and the dark hue indicates strength.

The results of Wavelet conversion of the HRV substantially coincided with each other in both the case of the measurement by the microwave and the case of the measurement by the electrocardiograph, thus revealing that the stress assessment could be made in the same manner.

It is apparent from the foregoing that the process of making the spectrum estimation based on the MEM for the phase difference signal as obtained permits to obtain the heartbeat frequency with a high accuracy, even in measurement, which is made with the use of the microwave in a non-contact state with the subject in a non-quiescent environment, and the stress assessment utilizing the HRV obtained from the heartbeat frequency can be made without causing any problem with the similar accuracy to that based on the HRV as obtained based on the measurement by the electrocardiograph.

REFERENCE SIGNS LIST 1 system for measuring a peak frequency of a signal
11 electromagnetic wave transmitting and receiving unit
11a antenna
11b microwave oscillator
11c directional coupler
11d attenuator
11e amplifier
11f circulator
11g quadrature detector
11h calculation section
12 signal analysis unit
13 conversion unit
50 treadmill
60 walkway
70 subject
80 person

What is claimed is:

1. A system for measuring a peak frequency of a signal for analyzing condition of a subject, which comprises:
an electromagnetic wave transmitting and receiving unit that irradiates a continuous electromagnetic wave having a predetermined frequency to a subject, receives a reflected wave from the subject, and outputs a phase difference signal between an irradiation wave and the reflected wave; and
a signal analysis unit that obtains, with a spectrum estimation utilizing a Maximum Entropy Method with a predetermined analysis duration, a frequency indicative of a occurrence frequency of a peak component of a signal, which is included by the phase difference signal between said irradiation wave and the reflected wave, and is generated substantially periodically in accordance with substantially a stationary change of the subject to be measured, and conducts repeatedly a process of calculating said frequency on a time axis of the phase difference signal.

2. The system for measuring the peak frequency of the signal for analyzing condition of the subject, as claimed in claim 1, comprises:
a conversion unit to which the frequency of said peak component calculated by said signal analysis unit is input, and which derives an occurrence time interval of the peak component based on a reciprocal of said frequency.

3. The system for measuring the peak frequency of the signal for analyzing condition of the subject, as claimed in claim 1, wherein:
said signal analysis unit conducts repeatedly the spectrum estimation with said analysis duration relative to said phase difference signal, while shifting, in each spectrum estimation, sequentially an analysis range by a predetermined shifted time from a signal start side toward a direction of a passage of time.

4. The system for measuring the peak frequency of the signal for analyzing condition of the subject, as claimed in claim 3, wherein:
said signal analysis unit sets, for a predetermined frequency range provided as a frequency bandwidth required for an evaluation with a frequency analysis to be conducted subsequently for the peak component of the signal to be measured, which has been derived by said signal analysis unit, said shifted time as a maximally long period of time within a range of time, which is obtained as a reciprocal of a frequency higher than twice a highest frequency in said predetermined frequency range.

5. The system for measuring the peak frequency of the signal for analyzing condition of the subject, as claimed in claim 1, wherein:
said signal analysis unit obtains a frequency power spectrum with the spectrum estimation with said analysis duration by the Maximum Entropy Method, and determines, as a frequency of said peak component to be obtained, a frequency having a maximum peak value in a known frequency range of said frequency power spectrum, said frequency having the maximum peak value corresponding to a frequency bandwidth of the peak component to be measured, which is actually applicable.

6. The system for measuring the peak frequency of the signal for analyzing condition of the subject, as claimed in claim 5, wherein:
said signal analysis unit conducts the spectrum estimation utilizing the Maximum Entropy Method for said phase difference signal, by estimating an auto-regressive model of the peak component to be measured, setting an auto-regressive model order as a value within a predetermined range and conducting a spectrum estimation based on said model;
said signal analysis unit previously conducts a simulation utilizing a signal model including an ideal peak component to determine at least a minimum value of a range of said model order;
the simulation utilizing the signal model including said ideal peak component is conducted by:
providing a plurality of patterns of the signal model having respectively different peak frequencies by adding the peak frequency in the model signal, which has a time window of a predetermined period of time and includes the ideal peak component to be measured, in a plurality of frequencies in a shifted manner by a predetermined frequency within the known frequency range corresponding to the frequency bandwidth of the peak component to be measured, which is actually applicable;
providing a plurality of analysis durations during which the spectrum estimation is to be applied, said analysis durations being different from each other within a range of said time window; and
conducting the respective spectrum estimation while using a number of data point, which is a product of the analysis duration and a sampling frequency, as a maximum value of the model order and varying the model order from 1 to a maximum value in a combination of each the signal model and each the analysis duration, detecting an existence of a spectrum peak in the known frequency range corresponding to the frequency bandwidth of the peak component to be measured, which is actually applicable, and determining, as an effective model order, the model order in case where the spectrum peak exists; and
said signal analysis unit determines, as a minimum value within a range of the model order as provided, which is to be used in the spectrum estimation with respect to said phase difference signal, a maximum one throughout all of minimum vales of the effective model orders in the respective combination of each the signal model and each the analysis duration, as obtained by said simulation.

7. The system for measuring the peak frequency of the signal for analyzing condition of the subject, as claimed in claim 6, wherein:

the spectrum peak existing in response to the effective model order in the simulation by said signal analysis unit is used as an estimated peak frequency of said model order;

said signal analysis unit calculates, for the effective model orders in the respective combination of each the signal model and each the analysis duration, as obtained by said simulation, an estimation error of the respective estimated peak frequency for the respective model orders relative to the frequency of the signal model, and extracts, as a representative model order, a minimum one of the model orders having the estimated peak frequencies in case where the estimation error becomes smallest;

the respective representative model orders are compiled for a same analysis duration and averaged, and an averaged value for the respective analysis duration is obtained as an averaged model order; and when the averaged model orders are represented in a two-dimensional graph in which the analysis duration is a first axis and the model order is a second axis, a value of the single model order forming a straight line, which is most approximate to a line indicative of the averaged model order on the graph, is used as an optimum value of the model order to be used in the spectrum estimation with respect to said phase difference signal.

8. The system for measuring the peak frequency of the signal for analyzing condition of the subject, as claimed in claim 5, wherein:

said signal analysis unit conducts the spectrum estimation utilizing the Maximum Entropy Method for said phase difference signal, by estimating an auto-regressive model of the peak component of the signal to be measured, setting an auto-regressive model order as a value within a predetermined range and conducting a spectrum estimation based on said model;

said signal analysis unit previously conducts a simulation utilizing a signal model including an ideal peak component to determine at least a lower value of a range of said model order;

the simulation utilizing the signal model including said ideal peak component is conducted by:

providing a plurality of patterns of the signal model having respectively different peak frequencies by adding the peak frequency in the model signal, which has a time window of a predetermined period of time and includes the ideal peak component to be measured, in a plurality of frequencies in a shifted manner by a predetermined frequency within the known frequency range corresponding to the frequency bandwidth of the peak component to be measured, which is actually applicable;

providing a plurality of analysis durations during which the spectrum estimation is to be applied, said analysis durations being different from each other within a range of said time window; and conducting the respective spectrum estimation while using a number of data point, which is a product of the analysis duration and a sampling frequency, as a maximum value of the model order and varying the model order from 1 to a maximum value in a combination of each the signal model and each the analysis duration, detecting an existence of a spectrum peak in the known frequency range corresponding to the frequency bandwidth of the peak component to be measured, which is actually applicable, and determining, as an effective model order, the model order in case where the spectrum peak exists; and said signal analysis unit determines, as a boundary value, a value of the analysis duration having a maximum value in the combination of the respective signal model in which no effective model order has been determined, and the respective analysis duration, as obtained by said simulation, and sets the range of the analysis duration in the spectrum estimation with respect to said phase difference signal so as to be larger than said boundary value.

9. The system for measuring the peak frequency of the signal for analyzing condition of the subject, as claimed in claim 1, wherein:

the peak component of the signal to be measured represents a heartbeat of the subject; and the frequency bandwidth of the peak component to be measured, which is actually applicable, is within a range of frequency from 0.7 Hz to 1.5 Hz, between which the heartbeat at rest in a sitting posture actually exists.

* * * * *